United States Patent
Dempsey

(10) Patent No.: US 12,090,343 B2
(45) Date of Patent: Sep. 17, 2024

(54) ASSESSMENT AND IMPROVEMENT OF TREATMENT USING IMAGING OF PHYSIOLOGICAL RESPONSES TO RADIATION THERAPY

(71) Applicant: ViewRay Systems, Inc., Denver, CO (US)

(72) Inventor: James F. Dempsey, Atherton, CA (US)

(*) Notice: Subject to any disclaimer, the term of this patent is extended or adjusted under 35 U.S.C. 154(b) by 266 days.

(21) Appl. No.: 17/346,109

(22) Filed: Jun. 11, 2021

(65) Prior Publication Data
US 2021/0308488 A1 Oct. 7, 2021

Related U.S. Application Data

(63) Continuation of application No. 16/116,312, filed on Aug. 29, 2018, now Pat. No. 11,040,222, which is a
(Continued)

(51) Int. Cl.
*A61N 5/10* (2006.01)
*A61B 5/00* (2006.01)
(Continued)

(52) U.S. Cl.
CPC .......... *A61N 5/1064* (2013.01); *A61B 5/0036* (2018.08); *A61B 5/055* (2013.01);
(Continued)

(58) Field of Classification Search
CPC .. A61N 5/1064; A61N 5/1048; A61N 5/1071; A61N 2005/1055; A61B 5/0036;
(Continued)

(56) References Cited

U.S. PATENT DOCUMENTS

| 3,428,307 A | 2/1969 | Hunter |
| 3,569,823 A | 3/1971 | Golay |
| (Continued) | | |

FOREIGN PATENT DOCUMENTS

| CN | 1394550 A | 2/2003 |
| CN | 1612713 A | 5/2005 |
| (Continued) | | |

OTHER PUBLICATIONS

Bennett et al., Severity of Baseline Magnetic Resonance Imaging-Evident Sacroiliitis and HLA-B27 Status in Early Inflammatory Back Pain Predict Radiographically Evident Ankylosing Spondylitis at Eight Years, Arthritis & Rheumatism, vol. 58, No. 11, Nov. 2008, pp. 3413-3418, DOI 10.1002/art.24024.*
(Continued)

*Primary Examiner* — Bo Joseph Peng
(74) *Attorney, Agent, or Firm* — Davis Graham & Stubbs LLP

(57) ABSTRACT

Edema in tissue of a patient undergoing a course of radiation therapy or treatment can be estimated based on one or more MRI measurements used to measure changes in fluid content of various tissues. A correlation between observed changes in edema and one or more delivered fractions of radiation can be used to drive one or more clinical actions. Methods, systems, articles of manufacture, and the like are described.

14 Claims, 9 Drawing Sheets

Related U.S. Application Data continuation of application No. 15/851,543, filed on Dec. 21, 2017, now Pat. No. 10,835,763, which is a continuation of application No. 14/064,053, filed on Oct. 25, 2013, now Pat. No. 9,889,318.

(60) Provisional application No. 61/719,337, filed on Oct. 26, 2012.

(51) Int. Cl.
  *A61B 5/055*    (2006.01)
  *G01R 33/50*    (2006.01)

(52) U.S. Cl.
  CPC .......... *A61B 5/4836* (2013.01); *A61B 5/4848* (2013.01); *A61B 5/4878* (2013.01); *G01R 33/50* (2013.01); *A61N 5/1048* (2013.01); *A61N 2005/1055* (2013.01); *A61N 5/1071* (2013.01)

(58) Field of Classification Search
  CPC ..... A61B 5/055; A61B 5/4836; A61B 5/4848; A61B 5/4878; G01R 33/50
  See application file for complete search history.

(56) References Cited

U.S. PATENT DOCUMENTS

| | | |
|---|---|---|
| 3,735,306 A | 5/1973 | Kabler |
| 4,019,059 A | 4/1977 | Brundin |
| 4,233,662 A | 11/1980 | Lemay |
| 4,481,657 A | 11/1984 | Larsson |
| 4,589,126 A | 5/1986 | Augustsson |
| 4,642,569 A | 2/1987 | Hayes |
| 4,652,826 A | 3/1987 | Yamamoto |
| 4,740,753 A | 4/1988 | Glover |
| 4,771,785 A | 9/1988 | Duer |
| 4,851,778 A | 7/1989 | Kaufman |
| 4,987,309 A | 1/1991 | Klasen |
| 5,006,804 A | 4/1991 | Dorri |
| 5,027,818 A | 7/1991 | Bova |
| 5,039,867 A | 8/1991 | Nishihara |
| 5,117,829 A | 6/1992 | Miller |
| 5,280,428 A | 1/1994 | Wu |
| 5,295,488 A | 3/1994 | Lloyd |
| 5,327,884 A | 7/1994 | Hardy |
| 5,328,681 A | 7/1994 | Kito |
| 5,331,552 A | 7/1994 | Lloyd |
| 5,361,763 A | 11/1994 | Kao |
| 5,365,927 A | 11/1994 | Roemer |
| 5,373,239 A | 12/1994 | Marek |
| 5,377,678 A | 1/1995 | Dumoulin |
| 5,378,989 A | 1/1995 | Barber |
| 5,391,139 A | 2/1995 | Edmundson |
| 5,412,823 A | 5/1995 | Sitta |
| 5,443,068 A | 8/1995 | Cline |
| 5,511,549 A | 4/1996 | Legg |
| 5,530,352 A | 6/1996 | Kolem |
| 5,547,454 A | 8/1996 | Horn |
| 5,585,724 A | 12/1996 | Morich |
| 5,592,091 A | 1/1997 | Manabe |
| 5,647,361 A | 7/1997 | Damadian |
| 5,675,305 A | 10/1997 | Demeester |
| 5,722,411 A | 3/1998 | Suzuki |
| 5,760,582 A | 6/1998 | Morrone |
| 5,790,996 A | 8/1998 | Narfstrom |
| 5,952,830 A | 9/1999 | Petropoulos |
| 5,993,373 A | 11/1999 | Nonaka |
| 6,005,916 A | 12/1999 | Johnson |
| 6,094,760 A | 8/2000 | Nonaka |
| 6,125,335 A | 9/2000 | Simon |
| 6,157,278 A | 12/2000 | Katznelson |
| 6,207,952 B1 | 3/2001 | Kan |
| 6,273,858 B1 | 8/2001 | Fox |
| 6,311,389 B1 | 11/2001 | Uosaki |
| 6,320,377 B1 | 11/2001 | Miyazaki |
| 6,405,072 B1 | 6/2002 | Cosman |
| 6,459,769 B1 | 10/2002 | Cosman |
| 6,509,735 B2 | 1/2003 | Mueller |
| 6,512,942 B1 | 1/2003 | Burdette |
| 6,591,127 B1 | 7/2003 | Mckinnon |
| 6,636,645 B1 | 10/2003 | Yu |
| 6,788,060 B1 | 9/2004 | Feenan |
| 6,806,712 B2 | 10/2004 | Akgun |
| 6,891,924 B1 | 5/2005 | Yoda |
| 6,940,281 B2 | 9/2005 | Feenan |
| 6,954,068 B1 | 10/2005 | Takamori |
| 7,092,573 B2 | 8/2006 | Luo |
| 7,202,663 B2 | 4/2007 | Huang |
| 7,230,429 B1 | 6/2007 | Huang |
| 7,265,545 B2 | 9/2007 | Krueger |
| 7,308,298 B2 | 12/2007 | Miyazaki |
| 7,453,264 B2 | 11/2008 | Trequattrini |
| 7,489,131 B2 | 2/2009 | Lvovsky |
| 7,532,705 B2 | 5/2009 | Yin |
| 7,535,229 B2 | 5/2009 | Schlueter |
| 7,542,622 B1 | 6/2009 | Angelini |
| 7,659,718 B1 | 2/2010 | Lustig |
| 7,791,338 B2 | 9/2010 | Kim |
| 7,840,045 B2 | 11/2010 | Guo |
| 7,901,357 B2 | 3/2011 | Boctor |
| 8,155,417 B2 | 4/2012 | Piron |
| 8,310,233 B2 | 11/2012 | Trzasko |
| 8,334,697 B2 | 12/2012 | Overweg |
| 8,378,677 B2 | 2/2013 | Morich |
| 8,570,042 B2 | 10/2013 | Pines |
| 8,637,841 B2 | 1/2014 | Prince |
| 8,803,524 B2 | 8/2014 | Dempsey |
| 8,812,077 B2 | 8/2014 | Dempsey |
| 8,896,308 B2 | 11/2014 | Shvartsman |
| 8,981,779 B2 | 3/2015 | Shvartsman |
| 9,082,520 B2 | 7/2015 | Prince |
| 9,289,626 B2 | 3/2016 | Kawrakow |
| 9,421,398 B2 | 8/2016 | Shvartsman |
| 9,423,477 B2 | 8/2016 | Dempsey |
| 9,446,263 B2 | 9/2016 | Dempsey |
| 9,472,000 B2 | 10/2016 | Dempsey |
| 9,498,167 B2 | 11/2016 | Mostafavi |
| 9,526,918 B2 | 12/2016 | Kruip |
| 9,675,271 B2 | 6/2017 | Shvartsman |
| 10,613,171 B2 | 4/2020 | Li |
| 11,378,629 B2 | 7/2022 | Dempsey |
| 2001/0001807 A1 | 5/2001 | Green |
| 2001/0010464 A1 | 8/2001 | Takamori |
| 2001/0013779 A1 | 8/2001 | Marek |
| 2001/0022515 A1 | 9/2001 | Yamashita |
| 2002/0131556 A1 | 9/2002 | Steinberg |
| 2002/0151786 A1 | 10/2002 | Shukla |
| 2002/0193685 A1 | 12/2002 | Mate |
| 2003/0011451 A1 | 1/2003 | Katznelson |
| 2003/0068097 A1 | 4/2003 | Wilson |
| 2003/0086526 A1 | 5/2003 | Clark |
| 2003/0094947 A1 | 5/2003 | Akgun |
| 2003/0112107 A1 | 6/2003 | Forbes |
| 2003/0112922 A1 | 6/2003 | Burdette |
| 2003/0197507 A1 | 10/2003 | Liu |
| 2004/0026162 A1 | 2/2004 | Christen |
| 2004/0054248 A1 | 3/2004 | Kimchy |
| 2004/0106869 A1 | 6/2004 | Tepper |
| 2004/0239327 A1 | 12/2004 | Heid |
| 2005/0020917 A1 | 1/2005 | Scherch |
| 2005/0030028 A1 | 2/2005 | Clarke |
| 2005/0077899 A1 | 4/2005 | Jacobs |
| 2005/0180544 A1 | 8/2005 | Sauer |
| 2005/0197654 A1 | 9/2005 | Edman |
| 2005/0207531 A1 | 9/2005 | Dempsey |
| 2006/0033496 A1 | 2/2006 | Shvartsman |
| 2006/0120583 A1 | 6/2006 | Dewaele |
| 2006/0170679 A1 | 8/2006 | Wang |
| 2006/0280287 A1 | 12/2006 | Esham |
| 2006/0291621 A1 | 12/2006 | Yan |
| 2007/0038058 A1 | 2/2007 | West |
| 2007/0043286 A1 | 2/2007 | Weiguo |
| 2007/0052420 A1 | 3/2007 | Speck |

(56) References Cited

U.S. PATENT DOCUMENTS

| | | |
|---|---|---|
| 2007/0053492 A1 | 3/2007 | Kidani |
| 2007/0083114 A1 | 4/2007 | Yang |
| 2007/0230770 A1 | 10/2007 | Kulkarni |
| 2008/0024130 A1 | 1/2008 | Schlueter |
| 2008/0033287 A1 | 2/2008 | Schwarze |
| 2008/0049896 A1 | 2/2008 | Kuduvalli |
| 2008/0116894 A1 | 5/2008 | Weiger |
| 2008/0123927 A1 | 5/2008 | Miga |
| 2008/0197842 A1 | 8/2008 | Lustig |
| 2008/0235052 A1 | 9/2008 | Node-Langlois |
| 2009/0039886 A1 | 2/2009 | White |
| 2009/0129659 A1 | 5/2009 | Deutschmann |
| 2009/0147916 A1 | 6/2009 | Fallone |
| 2009/0161826 A1 | 6/2009 | Gertner |
| 2009/0171184 A1 | 7/2009 | Jenkins |
| 2010/0049030 A1 | 2/2010 | Saunders |
| 2010/0056900 A1 | 3/2010 | Whitcomb |
| 2010/0119032 A1 | 5/2010 | Yan |
| 2010/0312095 A1 | 12/2010 | Jenkins |
| 2010/0312100 A1 | 12/2010 | Zarkh |
| 2011/0024625 A1 | 2/2011 | Ehringfeld |
| 2011/0156703 A1 | 6/2011 | O'Connor |
| 2011/0204262 A1 | 8/2011 | Pu |
| 2011/0304416 A1 | 12/2011 | Warner |
| 2012/0019246 A1 | 1/2012 | Kannengiesser |
| 2012/0043482 A1 | 2/2012 | Prince |
| 2012/0070056 A1 | 3/2012 | Krueger |
| 2012/0230462 A1 | 9/2012 | Robar |
| 2012/0245453 A1 | 9/2012 | Tryggestad |
| 2013/0086163 A1 | 4/2013 | Neff |
| 2013/0090547 A1 | 4/2013 | Bani-Hashemi |
| 2013/0141094 A1 | 6/2013 | Miyazaki |
| 2013/0147476 A1 | 6/2013 | Shvartsman |
| 2013/0225975 A1 | 8/2013 | Harvey |
| 2013/0245425 A1 | 9/2013 | Dempsey |
| 2013/0261429 A1 | 10/2013 | Lee |
| 2013/0261430 A1 | 10/2013 | Uhlemann |
| 2013/0345545 A1 | 12/2013 | Gross |
| 2014/0010355 A1 | 1/2014 | Seeber |
| 2014/0077098 A1 | 3/2014 | Tachikawa |
| 2014/0084926 A1 | 3/2014 | Amthor |
| 2014/0128719 A1 | 5/2014 | Longfield |
| 2014/0263990 A1 | 9/2014 | Kawrykow |
| 2015/0002150 A1 | 1/2015 | Weissler |
| 2015/0126850 A1 | 5/2015 | Cetingul |
| 2015/0251020 A1 | 9/2015 | Calone |
| 2015/0273239 A1 | 10/2015 | Hsu |
| 2015/0346304 A1 | 12/2015 | Hu |
| 2016/0011288 A1 | 1/2016 | Overweg |
| 2016/0067525 A1 | 3/2016 | Bouchet |
| 2016/0232690 A1 | 8/2016 | Ahmad |
| 2016/0252596 A1 | 9/2016 | Nielsen |
| 2016/0256712 A1 | 9/2016 | Vahala |
| 2016/0278719 A1 | 9/2016 | Jensen |
| 2016/0334479 A1 | 11/2016 | Poole |
| 2016/0356869 A1 | 12/2016 | Dempsey |
| 2017/0065830 A1 | 3/2017 | Vahala |
| 2017/0120075 A1 | 5/2017 | Overweg |
| 2017/0148536 A1 | 5/2017 | Kawrykow |
| 2017/0176556 A1 | 6/2017 | Shvartsman |
| 2017/0203126 A1 | 7/2017 | Dempsey |
| 2017/0371001 A1 | 12/2017 | Dempsey |
| 2018/0003789 A1 | 1/2018 | Amthor |
| 2018/0280733 A1 | 10/2018 | Weidlich |
| 2019/0004131 A1 | 1/2019 | Wachowicz |
| 2019/0060670 A1 | 2/2019 | Ni |
| 2019/0090777 A1 | 3/2019 | Leghissa |
| 2019/0168028 A1 | 6/2019 | Dempsey |
| 2019/0217126 A1 | 7/2019 | Shvartsman |
| 2019/0353724 A1 | 11/2019 | Snelten |
| 2019/0353725 A1 | 11/2019 | Dempsey |
| 2020/0041587 A1 | 2/2020 | Findeklkee |
| 2020/0086143 A1 | 3/2020 | Maltz |
| 2020/0147412 A1 | 5/2020 | Ni |
| 2020/0230439 A1 | 7/2020 | Liu |
| 2020/0246637 A1 | 8/2020 | Wang |

FOREIGN PATENT DOCUMENTS

| | | |
|---|---|---|
| CN | 1669599 A | 9/2005 |
| CN | 1946339 A | 4/2007 |
| CN | 101000689 A | 7/2007 |
| CN | 101267858 A | 9/2008 |
| CN | 101268474 A | 9/2008 |
| CN | 101278361 A | 10/2008 |
| CN | 101309726 A | 11/2008 |
| CN | 101443819 A | 5/2009 |
| CN | 101452065 A | 6/2009 |
| CN | 102247658 A | 11/2011 |
| CN | 102369529 A | 3/2012 |
| CN | 102713682 A | 10/2012 |
| DE | 3828639 A1 | 3/1989 |
| EP | 0152554 A2 | 8/1985 |
| EP | 2230530 A1 | 9/2010 |
| EP | 2424430 B1 | 1/2013 |
| JP | 63294839 | 12/1988 |
| JP | H03243877 A | 10/1991 |
| JP | 06054916 | 1/1994 |
| JP | H07148142 A | 6/1995 |
| JP | H07213507 A | 8/1995 |
| JP | 2004351207 A | 12/2004 |
| JP | 2006149560 A | 6/2006 |
| JP | 2008194449 | 8/2008 |
| JP | 2008532681 A | 8/2008 |
| JP | 2009112870 A | 5/2009 |
| JP | 2009160308 | 7/2009 |
| JP | 2010269067 A | 12/2010 |
| JP | 2014502541 | 2/2014 |
| JP | 2015516259 | 6/2015 |
| JP | 6224020 | 7/2015 |
| JP | 2015520631 | 7/2015 |
| JP | 2016513560 | 5/2016 |
| WO | 1993018707 | 9/1993 |
| WO | 2000025864 | 5/2000 |
| WO | 2006097864 A1 | 9/2006 |
| WO | 2007012933 A2 | 2/2007 |
| WO | 2007014105 A2 | 2/2007 |
| WO | 2007126842 A2 | 11/2007 |
| WO | 2008122899 A1 | 10/2008 |
| WO | 2009004521 A2 | 1/2009 |
| WO | 2009107005 A2 | 9/2009 |
| WO | 2010113050 A2 | 10/2010 |
| WO | 2011063342 A1 | 5/2011 |
| WO | 2012045153 | 4/2012 |
| WO | 2015085008 A1 | 6/2015 |
| WO | 2015138945 | 9/2015 |
| WO | 20150138945 | 9/2015 |

OTHER PUBLICATIONS

Long et al., Bone Marrow Signal Alteration in the Spine and Sacrum, American Journal of Roentgenology. 2010;195: W178-W200. 10.2214/AJR.09.4134.*

Verhaert et al., Direct T2 Quantification of Myocardial Edema in Acute Ischemic Injury, JACC Cardiovasc Imaging. Mar. 2011; 4(3): 269-278. doi:10.1016/j.jcmg.2010.09.023.*

Neema et al., 3T MRI relaxometry detects T2 prolongation in the cerebral normal-appearing white matter in multiple sclerosis, Neuroimage. Jul. 1, 2009; 46(3): 633-641. doi:10.1016/j.neuroimage.2009.03.001.*

Mutic Sasa et al: "The ViewRay System: Magnetic Resonance-Guided and Controlled Radiotherapy", Seminars in Radiation Oncology, vol. 24, No. 3, Jun. 12, 2014 (Jun. 12, 2014), pp. 196-199.

PCT App. No. PCT/2018/063108; International Search Report and Written Opinion mailed May 10, 2019; 14 pages.

Green et al. 'Split cylindrical gradient coil for combined PET-MR system.' Proc. Intl. Soc. Mag. Reson. Med. 16 (2008):352.

Lucas et al. 'Simultaneous PET-MR: toward a combined microPET. RTM.-MR system.' Proc. Intl. Soc. Mag. Reson. Med. 15(2007):922.

(56) References Cited

OTHER PUBLICATIONS

Shvartsman et al. 'Gradient Coil Induced Eddy Current Computation Using the Boundary Elements Method.' Proc. Intl. Soc. Mag. Reson. Med. 17(2009):3055.

International Search Report issued by the European Patent Office in International Application No. PCT/US2014/023556 mailed Jul. 18, 2014. 6 pages.

AU App. No. 2017200361; Notice of Acceptance dated Oct. 30, 2018 (pp. 1-3).

Hong Pan, et al., Review; New and Emerging Techniques for Mapping Brain Circuitry; (2011) 67 ESBRR 1-2 226-251.

Mathieu Sarracanie et al: "Low Cost High Performance MRI", Proceedings of the International Society for Magnetic Resonance in Medicine, vol. 23, 702, May 15, 2015.

Noel C et al: "TU-G-217A-09: Feasibility of Bowel Tracking Using Onboard Cine MRI for Gated Radiotherapy", Medical Physics, Jun. 28, 2012 (Jun. 28, 2012), pp. 1-2, XP55832625, Retrieved from the Internet: URL:https://aapm.onlinelibrary.wiley.com/doi/abs/10.1118/1.

Barth, et al. "Simultaneous Multislice (SMS) Imaging Techniques." Magnetic Resonance in Medicine; vol. 75; pp. 63-81; 2016.

Bilgin, A. et al. 'Randomly Perturbed Radial Trajectories for Compressed Sensing MRI.' Proceedings of International Society for Magnetic Resonance in Medicine 16 (2008): p. 3152.

Blaimer, et al. 'Smash, Sense, Pills, Grappa, How to Choose the Optimal Method'. Top Magan Reson Imaging, vol. 15, No. 4, Aug. 2004, pp. 223-236.

Candes, et al. 'Robust Uncertainty Principles: Exact Signal Reconstruction from Highly Incomplete Frequency Information.' IEEE Transactions on Information Theory, vol. 52, No. 2, Feb. 2006, pp. 489-509.

Candes, et al. 'Sparsity and Incoherence in Compressive Sampling'. Electrical and Computer Engineering, Georgia Tech, Atlanta, GA, 90332. Nov. 2006, pp. 1-20.

CIPRA 'L1-magic' from SIAM News, vol. 39, No. 9, Nov. 2006. (3 pages).

Donoho, David L., 'Compressed Sensing'. Department of Statistics, Stanford University. Sep. 14, 2004. (34 pages).

EP App. No. 17000760.3; Extended EP Search Report mailed Nov. 9, 2017; 7 pages.

Extended European Search Report in European Patent Application No. EP11850577, dated Jul. 9, 2014. 8 pages.

Foroosh, Hassan, et.al. 'Extension of Phase Correlation to Subpixel Registration.' IEEE Transactions on Image Processing, vol. 11, No. 3, 2002, pp. 188-200.

Gerganov G et al, 'Portal image registration using the phase correlation method', 2013 IEEE Nuclear Science Symposium and Medical Imaging Conference (2013 NSS/MIC), IEEE, (Oct. 27, 2013), doi:10.1109/NSSMIC.2013.6829306, pp. 1-3, XP032601397.

Haacke, Mark E. et al. 'Constrained reconstruction: A superresolution, optimal signal-to-noise alternative to the Fourier transform in magnetic resonance imaging.' Medical Physics, AIP, Melville, NY, US, vol. 16, No. 3, May 1, 1989 (May 1, 1989), pp. 388-397, XP000034068, ISSN: 0094-2405, DDI: 10.1118/1.596427.

Hernando, D. et al. 'Interventional MRI with sparse sampling: an application of compressed sensing.' Proceedings of International Society for Magnetic Resonance in Medicine. 16 (2008): p. 1482.

Hong J et al, 'Interventional navigation for abdominal therapy based on simultaneous use of MRI and ultrasound', Medical and Biological Engineering and Computing, Springer, Heildelberg, DE, vol. 44, No. 12, doi:10.1007/S11517-006-0133-2, ISSN 0140-0118, (Nov. 11, 2006), pp. 1127-1134, (Nov. 11, 2006), XP001551805.

International Search Report and Written Opinion dated Apr. 13, 2012, for corresponding international application No. PCT/US2011/066605; 9 pages.

International Search Report of the International Searching Authority issued in International Application No. PCT/JS2014/028792, mailed Jul. 2, 2014. 3 pages.

Iarrazabal, Pablo, and Dwight G. Nishimura. 'Fast Three Dimensional Magnetic Resonance Imaging.' Magnetic Resonance in Medicine, vol. 33, No. 5, 1995, pp. 656-662.

Law, C. , and Glover, G. 'Deconvolving Haemodynamic Response Function in fMRI under high noise by Compressive Sampling.' Proceedings of International Society for Magnetic Resonance in Medicine. 17 (2009): p. 1712. Stanford University, Stanford, CA, United States.

Li, Kang and Kanadae, Takeo. "Nonnegative Mixed-Norm Preconditioning for Microscopy Image Segmentation." Information Processing in Medical Imaging. Springer Berlin Heidelberg. vol. 5636. (2009):362-373.

Lustig, et al. 'L1 SPIR-IT: Autocalibrating Parallel Imaging Compressed Sensing.' Electrical Engineering, Stanford University, Stanford, CA, United States. Radiology, Stanford University. Statistics, Stanford University (p. 334).

Lustig, M, et. al. 'Faster Imaging with Randomly Perturbed, Undersampled Spirals and |L|_1 Reconstruction.' In: Proceedings of the 13th Annual Meeting of ISMRM, Miami Beach, 2005. (1 page).

Macura, Katarzyna J., MD, PhD. 'Advancements in Magnetic Resonance-Guided Robotic Interventions in the Prostate'. Top Magn Reson Imaging. vol. 19, No. 6. Dec. 2008. pp. 297-304.

Medtronic, Inc.. 'Image-Guided Surgery Overview'. 2010. 2 pages.

Meyer, et al. "Fast Spiral Coronary Artery Imaging", Magnetic Resonance in Medicine 28, pp. 202-213 (1992).

Mozer, Pierre C, MD, PhD. 'Robotic Image-Guided Needle Interventions of the Prostate'. Reviews in Urology. vol. 11, No. 1. 2009. pp. 7-15.

Muntener, Michael, MD et al. 'Transperineal Prostate Intervention: Robot for fully Automated MR Imaging-System Description and Proof of Principle in a Canine Model'. Radiology. vol. 247, No. 2. May 2008. pp. 543-549.

Partial International Search Report Issued in International Application No. PCT/US2013/039009, mailed Oct. 18, 2013. 2 pages.

Patriciu, Alexandru, et al., 'Automatic Brachytherapy Seed Placement Under MRI Guidance'. IEEE Transactions on Biomedical Engineering. vol. 54, No. 8. Aug. 2007. pp. 1-8.

PCT App. No. PCT/US2010/039036; International Search Report mailed Aug. 11, 2010; (pp. 1-2).

PCT App. No. PCT/US2017/038867; International Search Report and Written Opinion mailed Nov. 8, 2017; (pp. 1-12).

Reddy, B. Srinivasa, and B. N. Chatterji. 'An FFT-Based Technique for Translation, Rotation, and Scale-Invariant Image Registration.' IEEE Transactions on Image Processing, vol. 5, No. 8, Aug. 1996, pp. 1266-1271.

Riek, et al. "Flow Compensation in MRI Using a Phase-Corrected Real Reconstruction", Magnetic Resonance in Medicine 30, pp. 724-731, 1993.

Roullot Elodie et al. 'Regularized reconstruction of 3D high-resolution magnetic resonance images from acquisitions of anisotropically degraded resolutions.' Pattern Recognition, 2000. Proceedings. 15TH International Conference on Sep. 3-7, 2000; [Proceedings of the International Conference on Pattern Recognition. (ICPR)], Los Alamitos, CA, USA, IEEE Comput. SOC, US, vol. 3, Sep. 3, 2000 (Sep. 3, 2000), pp. 346-349.

Stoianovici, Dan, et al. MRI Stealth' Robot for Prostate Interventions'. Minimally Invasive Therapy. 2007. pp. 241-248.

Tokuda, J. et al. 'Real-Time Organ Motion Tracking and Fast Image Registration System for MRI-Guided Surgery.' Systems and Computers in Japan Scripta Technica USA. vol. 37, No. 1. Jan. 2006: 83-92. Database Inspec [Online]. The Institution of Electrical Engineers, Stevenage, GB; Jan. 2006.

Trzasko et al. 'Highly Undersampled Magnetic Resonance Image Reconstruction via Homotopic L0-Minimization' IEEE Transactions on Medical Imaging. vol 28. No. 1. Jan. 31. 2009, pp. 106-121.

Webb, Steve. "Historical Perspective on IMRT." Institute of Cancer Research and Royal Marsden NHS Trust. 2002. (23 pages).

Yang, Junfeng, et al. 'A Fast TVL1-L2 Minimization Algorithm for Signal Reconstruction from Rartial Fourier Data.' Technical Report, TR08-27, CAAM, Rice University Houston, TX, 2008. pp.1-10.

(56) References Cited

OTHER PUBLICATIONS

Zitova B et al, 'Image Registration Methods: A Survey', Image and Vision Computing, Elsevier, Guildford, GB, (Oct. 1, 2003), vol. 21, No. 11, doi:10.1016/S0262-8856(03)00137-9, ISSN 0262-8856, pp. 977-1000, XP001189327.

PCT App. No. PCT/US2016/063416; International Preliminary Report on Patentability and International Search Report with Written Option mailed Jun. 7, 2018; 9 pages.

Zaitsev M et al.: "Shared k-space Echo Planar Imaging with Keyhole," Magnetic Resonance in Medicine, John Wiley & Sons, Inc. US, vol. 45, Jan. 1, 2001, pp. 109-117, XP002311925, ISSN: 0740-3194.

B W Raaymakers et al.; "Integrating a 1.5 T Mri Scanner with a 6 MV Accelerator: Proof of Concepts," Physics in Medicine and Biology. vol. 54, No. 12, May 19, 2009, pp. N229-N237, XP055395399, Bristol GB ISSN: 0031-9155. 9 pages.

Jan J. W. Lagendijk et al.; "MR Guidance in Radiotherapy", Physics in Medicine and Biology, Institute of Physics Publishing, Bristol GB, vol. 59, No. 21, Oct. 16, 2014, pp. R349-R369, XP020272054, ISSN: 0031-9155.

Weaver, John B.; "Simultaneous Multislice Acquisition of MR Images", Magnetic Resonance in Medicine, John Wiley & Sons, Inc., vol. 8, No. 3, Nov. 1, 1988, pp. 275-284, XP000003030, ISSN: 0740-3194.

AU Search Report mailed Dec. 11, 2017; 2 pages.

Kwan-Jin JUNG, et al., "Parallel Imaging with Asymmetric Acceleration to Reduce Gibbs Artifacts and to Increase Signal-To-Noise Ratio of the Gradient Echo Echo-Planar Imaging Sequence for Functional MRI," Magnetic Resonance in Medicine 67:419-427 (2012).

Aytekin Oto, MD, et al., Multidetector Row CT of the Liver; (2005) 43 ERDCNA 5 827-848.

* cited by examiner

ASSESSMENT AND IMPROVEMENT OF TREATMENT USING IMAGING OF PHYSIOLOGICAL RESPONSES TO RADIATION THERAPY

CROSS-REFERENCE TO RELATED APPLICATIONS

The current application is a continuation of and claims priority under 35 U.S.C. § 120 to U.S. patent application Ser. No. 16/116,312, filed Aug. 29, 2018, which claims priority under 35 U.S.C. § 120 to U.S. patent application Ser. No. 15/851,543, filed Dec. 21, 2017, now U.S. Pat. No. 10,835,763, which claims priority under 35 U.S.C. § 120 to U.S. patent application Ser. No. 14/064,053, filed Oct. 25, 2013, now U.S. Pat. No. 9,889,318, which claims priority under 35 U.S.C. § 119(e) to U.S. Provisional Application 61/719,337, which was filed on Oct. 26, 2012, the disclosures of each are incorporated by reference in its entirety.

TECHNICAL FIELD

The subject matter described herein relates to radiation therapy and to MRI imaging of physiological responses to radiation therapy, such as for example edema, etc.

BACKGROUND

Radiation therapy maintains a unique and established role among the three major forms of cancer therapy (surgery, chemotherapy, and radiation therapy). Surgery removes cancer-laden tissues from the body, destroying them. Chemotherapy sterilizes microscopic disease throughout the entire body. Only radiation therapy can both destroy cancerous tissues and sterilize microscopic disease simultaneously. Experimental ablative cancer treatment technologies (e.g., ultrasound, hyperthermia, and cryosurgery) can only destroy tissue like surgery, while novel chemotherapy agents cannot effectively destroy solid tumors. Radiation therapy will maintain and expand its prominent role as the treatment of choice in cancer therapy and ablative therapies.

The clinical objective of radiation therapy is to accurately deliver an optimized ionizing radiation dose distribution to the tumor and targets while sparing the dose to the surrounding normal tissue. In delivering ionizing radiation, the clinician attempts to make a trade off between the probability that the disease will be eradicated and the probability that a deadly or debilitating side effect will occur from the irradiation of the surrounding healthy or functional tissues.

Whether ablating or sterilizing tissues, ionizing radiation kills cells by breaking chemical bonds in DNA or other important molecules in the cell. Radiation therapy functions by targeting rapidly dividing cancer cells, where the radiation causes a reaction that damages the DNA or other important molecules in the cell, causing cell death at cell division. Cancer cells, unlike normal cells, divide rapidly and can't repair themselves easily, and as a result of the genetic damage from the radiation, they die more readily than healthy cells. Extending the treatment over time and delivering the dose in fractions allows healthy cells to recover while tumor cells are preferentially eliminated. Sometimes, less recovery of healthy cells can be accepted if greater positioning and immobilization accuracy can be attained using stereotactic methods.

The use of ionizing radiation therapy to treat cancer or ablate tissues works by damaging the DNA or other critical molecules of cancerous or targeted cells. This DNA damage is caused when ionizing charged particles cause direct or indirect ionization of the atoms, which make up the DNA chain or other important cellular molecules. Direct ionization occurs when the atoms of DNA or other critical cellular molecules are directly produced by the impinging radiation. Indirect ionization occurs as a result of the ionization of the aqueous cellular component, forming free radicals, which then damage the DNA or other critical cellular molecules. Cells have mechanisms for repairing single-strand DNA damage and thus double-stranded DNA breaks are the most significant mechanism for causing cell death. Cancer cells are generally undifferentiated and stem cell-like, which causes them to reproduce more than most healthy differentiated cells, and also to have a diminished ability to repair sub-lethal damage. Single-strand DNA damage is then passed on through cell division and damage to the cancer cells' DNA accumulates, causing them to die or reproduce more slowly.

Radiosensitivity is the relative susceptibility of cells, tissues, organs or organisms to the harmful effect of ionizing radiation. There are four major modifiers of radiosensitivity, which are typically referred to as "4 R's": re-oxygenation, re-assortment of the cell-cycle, repair of sublethal damage, and repopulation.

Tumors contain regions of hypoxia (low aqueous oxygen concentration) in which cancer cells are thought to be resistant to radiation. During fractionated radiotherapy, these regions are reoxygenated by various mechanisms including reduction of intratumoral pressure and normalization of the vasculature. Reoxygenation between radiation fractions leads to radiosensitization of previously hypoxic tumor areas and is thought to increase the efficiency of radiation treatment.

Mammalian cells exhibit different levels of radioresistance during the course of the cell cycle. In general, radiation has a greater effect on cells with a greater reproductive activity. Cells in the late S-phase are especially resistant and cells in the G2-phase and M-phase are most sensitive to ionizing radiation. During fractionated radiation, cells in the G2M-phase are preferentially killed. The time between two fractions allows resistant cells from the S-phase of the cell cycle to redistribute into phases in which cells are more radiosensitive.

Cell kill by ionizing radiation is based on production of unrepairable lesions involving DNA double-strand breaks (DSBs) or damage of other critical molecules. Most radiation-induced DNA damage is however sublethal. Although this damage is generally repaired at lower doses, at higher doses accumulation of sublethal lesions also contributes to lethality. Repair of sublethal damage between radiation fractions is exploited in radiation therapy because critical normal tissues and tumors often differ in their ability to repair radiation damage.

Normal and malignant stem cells have the ability to perform asymmetric cell division, which results in a daughter stem cell and a committed progenitor cell. In contrast, stem cells divide into two committed progenitor cells or two daughter stem cells in a symmetric cell division. If the latter happens only in 1% of the stem cell divisions, the number of stem cells after 20 cell doublings will be twice as high as the number of committed progenitor cells. As such, small changes in the way stem cells divide can have a huge impact on the organization of a tissue or tumor and are thought to be the mechanism behind accelerated repopulation.

Quickly dividing tumor cells and tumor stem cells are generally (although not always) more sensitive than the majority of body cells. The 4 R's mentioned above can have a significant impact on the radiosensitivity of both tumor and healthy cells, which can be, for example, hypoxic and therefore less sensitive to X-rays that mediate most of their effects through free radicals produced by ionizing oxygen.

The most sensitive cells are those that are undifferentiated, well nourished, quickly dividing, and highly metabolically active. Amongst the body cells, the most sensitive are spermatogonia and erythroblasts, epidermal stem cells, and gastrointestinal stem cells. The least sensitive are nerve cells and muscle fibers. Very sensitive cells also include oocytes and lymphocytes, although they are resting cells and thus do not meet the criteria described above.

The damage of the cell can be lethal (the cell dies) or sublethal (the cell can repair itself). The effects on cells can be deterministic and/or stochastic.

Deterministic effects have a threshold of irradiation under which they do not appear and are the necessary consequence of irradiation. The damage caused by deterministic effects generally depends on the dose. Such effects are typically sublethal (e.g., they produce a less pronounced form of disease) in a dose rage between about 0.25 to 2 Sv (Sieverts), and lethal (e.g., a certain percent of the population dies within 60 days) in a dose rage between about 2 to 5 Sv. Dose above about 5 Sv cause the majority of people to die within 60 days, and those above 6 to 7 Sv cause all people to die. Of course, the specific effects on any one person also depend on other factors, such as for example age, sex, health etc.

Stochastic or random effects, which can be classified as either somatic or genetic effects, are coincidental and cannot be avoided. Such effects also do not have a threshold. Among somatic effects, secondary cancer is the most important. Secondary cancer generally develops because radiation causes DNA mutations directly and indirectly. Direct effects are those caused by ionizing particles and rays themselves, while the indirect are those that are caused by free radicals, generated especially in water radiolysis and oxygen radiolysis. The genetic effects confer the predisposition of cancer to the offspring.

The response of a type of cancer cell to radiation is described by its radiosensitivity. Highly radiosensitive cancer cells are rapidly killed by modest doses of radiation. Such cancer cells include leukemias, most lymphomas, and germ cell tumors. The majority of epithelial cancers are only moderately radiosensitive, and require a significantly higher dose of radiation, such as for example approximately 60 to 70 Gy (Grays) to achieve a radical cure. Some types of cancer are notably radioresistant, that is, much higher doses are required to produce a radical cure than may be safe in clinical practice. Renal cell cancer and melanoma are generally considered to be radioresistant.

The response of a tumor to radiation therapy can also be related to a size of the tumor. For complex reasons, very large tumors respond less well to radiation than smaller tumors or microscopic disease. Various strategies can be used to overcome this effect. The most common technique is surgical resection prior to radiation therapy. This approach is most commonly seen in the treatment of breast cancer with wide local excision or mastectomy followed by adjuvant radiation therapy. Another method involves shrinking the tumor with neoadjuvant chemotherapy prior to radical radiation therapy. A third technique involves enhancing the radiosensitivity of the cancer by giving certain drugs during a course of radiation therapy. Examples of radiosensitizing drugs include, but are not limited to Cisplatin, Nimorazole, Cetuximab, and the like.

Radiation therapy is itself painless to the patient. Many low-dose palliative treatments (for example, radiation therapy to bony metastases) cause minimal or no side effects, although short-term pain flare-up can be experienced in the days following treatment due to edema compressing nerves in the treated area. Higher doses can cause varying side effects during treatment (acute side effects), in the months or years following treatment (long-term side effects), or after re-treatment (cumulative side effects). The nature, severity, longevity, etc. of side effects depend on the radiosensitivity of organs that receive the radiation, the treatment itself (type of radiation, dose, fractionation, concurrent chemotherapy), and the patient. Side effects from radiation are usually limited to the area of the patient's body that is under treatment.

The major side effects observed in the current art of radiation therapy are fatigue and skin irritation. The fatigue often sets in during the middle of a course of treatment and can last for weeks after treatment ends. The irritated skin will heal, but may not be as elastic as it was before. Many acute side effects are also observed.

Acute side effects are induced either immediately or soon after commencement of irradiation. Such effects can include swelling (also referred to as edema or oedema), nausea and vomiting, damage to epithelial surfaces, mouth and throat sores, intestinal discomfort, infertility, and the like. Late effects occur months to years after treatment and are generally limited to the area that has been treated. They are often caused by damage of blood vessels and connective tissue cells. Severity of late effects can be reduced by fractionating treatment into smaller parts. The damaged and dying cells in an organ will signal and produce an inflammatory response to ionizing radiation, which is the underlying cause of many of the acute effect listed below.

As part of the general inflammation that occurs from radiation damage of cells, swelling of soft tissues may cause problems during radiation therapy. This acute effect can be a concern during treatment of brain tumors and brain metastases, especially where there is pre-existing raised intracranial pressure or where the tumor is causing near-total obstruction of a lumen (e.g., trachea or main bronchus). Surgical intervention may be considered prior to treatment with radiation. If surgery is deemed unnecessary or inappropriate, the patient may receive steroids during radiation therapy to reduce swelling.

Nausea and vomiting are typically associated only with treatment of the stomach or abdomen (which commonly react a few hours after treatment), or with radiation therapy to certain nausea-producing structures in the head during treatment of certain head and neck tumors, most commonly the vestibules of the inner ears. As with any distressing treatment, some patients vomit immediately during radiotherapy, or even in anticipation of it, but this is considered a psychological response. Nausea for any reason can be treated with antiemetics.

Epithelial surfaces may sustain damage from radiation therapy. Depending on the area being treated, this may include the skin, oral mucosa, pharyngeal, bowel mucosa, ureter, etc. The rates of onset of damage and recovery from such damage depend upon the turnover rate of epithelial cells. Typically, the skin starts to become pink and sore several weeks into treatment. This reaction may become more severe during the treatment and for up to about one week following the end of radiation therapy, and the skin may break down. Although this moist desquamation is uncomfortable, recovery is usually quick. Skin reactions tend to be worse in areas where there are natural folds in the skin, such as underneath the female breast, behind the ear, and in the groin.

If the head and neck area is treated, temporary soreness and ulceration can commonly occur in the mouth and throat. If severe, these effects can affect swallowing, and the patient may need painkillers and nutritional support/food supplements. The esophagus can also become sore if it is treated directly, or if, as commonly occurs, it receives a dose of collateral radiation during treatment of lung cancer.

The lower bowel may be treated directly with radiation (treatment of rectal or anal cancer) or be exposed by radiation therapy to other pelvic structures (prostate, bladder, female genital tract). Typical symptoms can include soreness, diarrhea, and nausea.

The gonads (ovaries and testicles) are very sensitive to radiation. They may be unable to produce gametes following direct exposure to most normal treatment doses of radiation. Treatment planning for all body sites is designed to minimize, if not completely exclude, dose to the gonads if they are not the primary area of treatment. Infertility can be efficiently avoided by sparing at least one gonad from radiation.

Over the long term, other morphological changes due to cell death and radiation denaturing or damaging of tissues will appear as late side effects, such as for example fibrosis, epilation, dryness, lymphedema, cancer, heart disease, cognitive decline, radiation proctitis, etc.

Fibrosis refers to irradiated tissues tending to become less elastic over time due to a diffuse scarring process. Epilation (hair loss) may occur on any hair bearing skin with doses above 1 Gy. It only occurs within the radiation field/s. Hair loss may be permanent with a single dose of 10 Gy, but if the dose is fractionated permanent hair loss may not occur until dose exceeds 45 Gy.

The salivary glands and tear glands have a radiation tolerance of about 30 Gy in 2 Gy fractions, a dose which is exceeded by most radical head and neck cancer treatments. Dry mouth (xerostomia) and dry eyes (xerophthalmia) can become irritating long-term problems and severely reduce the patient's quality of life. Similarly, sweat glands in treated skin (such as the armpit) tend to stop working, and the naturally moist vaginal mucosa is often dry following pelvic irradiation.

Lymphedema, a condition of localized fluid retention and tissue swelling, can result from damage to the lymphatic system sustained during radiation therapy. It is the most commonly reported complication in breast radiation therapy patients who receive adjuvant axillary radiotherapy following surgery to clear the axillary lymph nodes.

Radiation, while used to treat cancer, is at the same time a potential cause of cancer, and secondary malignancies are seen in a very small minority of patients—usually less than $\frac{1}{1000}$. Cancers resulting from radiation treatments typically arise 20 to 30 years following treatment, although some haematological malignancies may develop within 5 to 10 years. In the vast majority of cases, this risk is greatly outweighed by the reduction in risk conferred by treating the primary cancer. New cancers resulting from radiation treatment typically occur within the treated area of the patient.

Radiation has potentially excess risk of death from heart disease seen after some past breast cancer radiation therapy regimens.

In cases of radiation applied to the head radiation therapy may cause cognitive decline. Cognitive decline was especially apparent in young children, between the ages of 5 to 11. Studies found, for example, that the IQ of 5 year old children declined each year after treatment by several IQ points.

Radiation proctitis can involve long-term effects on the rectum, including one or more of bleeding, diarrhoea and urgency, and is generally associated with radiation therapy to pelvic organs. Pelvic radiation therapy can also cause radiation cystitis when the bladder is affected.

SUMMARY

In one aspect, a method includes comparing a subsequent edema analysis performed after or during at least part of a course of radiation treatment to a baseline edema analysis (performed previous to the subsequent edema analysis to estimate a change in edema in patient tissues resulting from the course of radiation treatment, deriving an edema to delivered dose correlation based at least in part on the change in edema in the patient tissue correlated with a delivered dose of radiation during the course of radiation treatment, and performing one or more clinical actions based on the edema to delivered dose correlation.

In some variations one or more of the following can optionally be included. The subsequent edema analysis and baseline edema analysis can each include at least one of an MRI scan, a $T_1$-weighted MRI scan, a $T_2$-weighted MRI scan, a ratio of $T_1$-weighted MRI to $T_1$-weighted MRI scan results, and an MRI response ratio. For example, the subsequent edema analysis can include a subsequent MRI scan and the baseline edema analysis comprises a baseline MRI scan. Alternatively or in addition, the subsequent edema analysis can include a subsequent ratio of a subsequent $T_1$-weighted scan and a subsequent $T_2$-weighted MRI scan and the baseline edema analysis comprises a ratio of a baseline $T_1$-weighted and a baseline $T_1$-weighted MRI scan.

The comparing can include quantifying changes in free hydrogen content in the patient tissues as a proxy for the change in edema, and the quantifying can include performing a differential analysis of the subsequent edema analysis and the baseline edema analysis to derive a relative amount of free hydrogen as a function of location in the patient tissue. The deriving of the edema to delivered dose correlation can include applying one or more calculations or models of physical dose delivery to derive one or more of an amount of radiation actually delivered to the patient tissue and an expected amount of radiation delivered to the patient tissue. The derived amount of radiation actually delivered or expected to have been delivered can be based at least in part on one or more inputs comprising a pre-radiation treatment plan and/or on a combined MRI and radiation delivery approach that calculates received doses of radiation based on intra-fraction motions of the patient tissue.

The method can further include correlating the change in edema in the patient tissue with the delivered dose. The correlating can include quantifying how the change in edema corresponds to an expected outcome for the diseased tissue and surrounding tissues relative to an expected value. The expected value can be calculated using at least one of empirical, experimental, and theoretical modeling approaches. The one or more clinical actions based on the edema to delivered dose correlation can include at least one of stopping the course of treatment for further analysis, alerting a clinician, increasing an amount of radiation delivered in a later fraction of the course of treatment, and reducing an amount of radiation delivered in the later fraction of the course of treatment.

Systems and methods consistent with this approach are described as well as articles that comprise a tangibly embodied machine-readable medium operable to cause one or more machines (e.g., computers, etc.) to result in operations described herein. Alternatively, hardware, including but not limited to digital electronic circuitry, integrated circuitry, specially designed application specific integrated circuits (ASICs), field programmable gate arrays (FPGAs) computer hardware, firmware, software, computing systems, and/or combinations thereof, can be configured to perform one or more operations described herein. A computing system may include a programmable processor, such as for example a general purpose processor and a memory coupled to the processor. The memory may include one or more programs that cause the programmable processor to perform one or more of the operations described herein.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
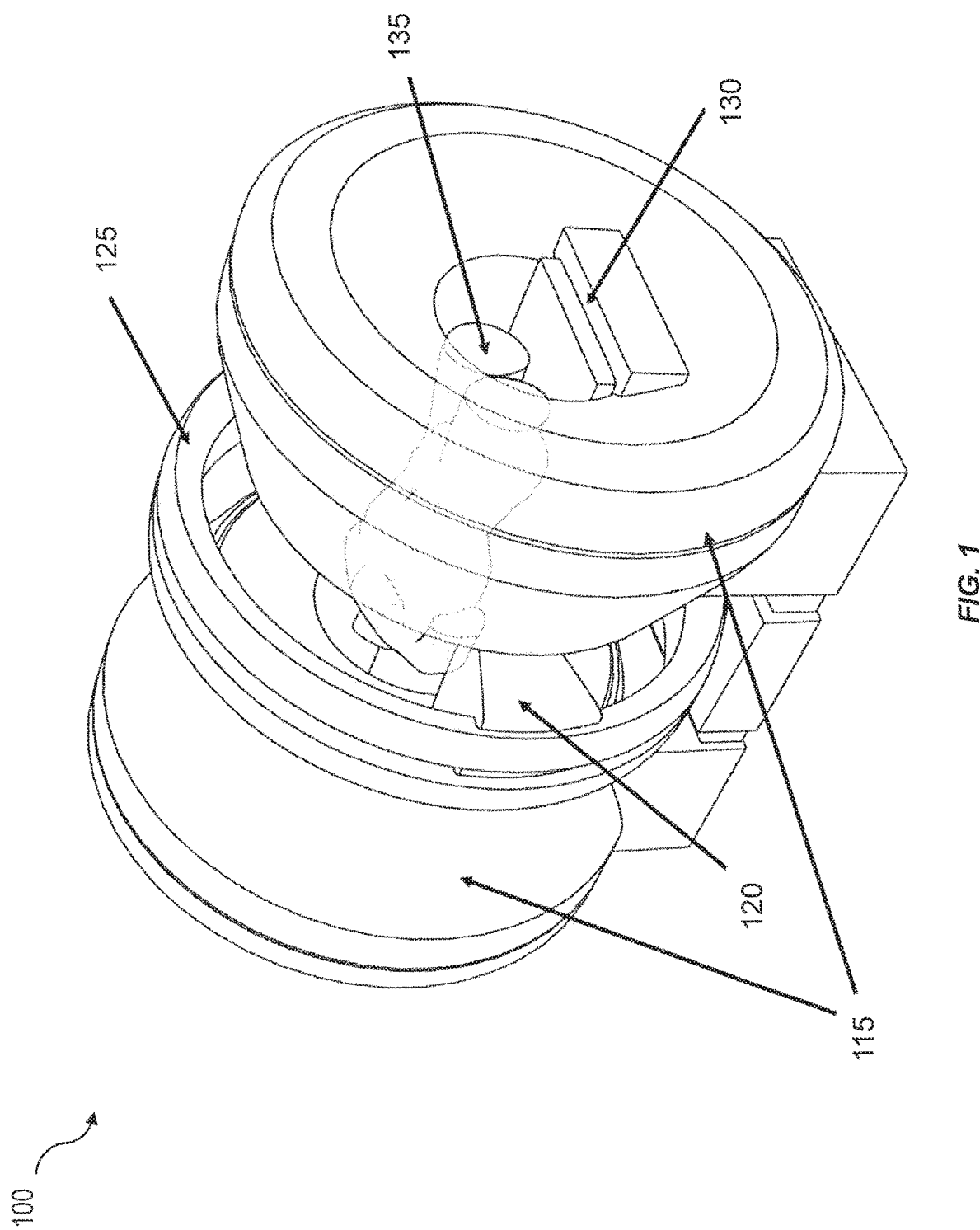
FIG. 1 shows a schematic diagram of a radiation therapy system.
Figure 2:
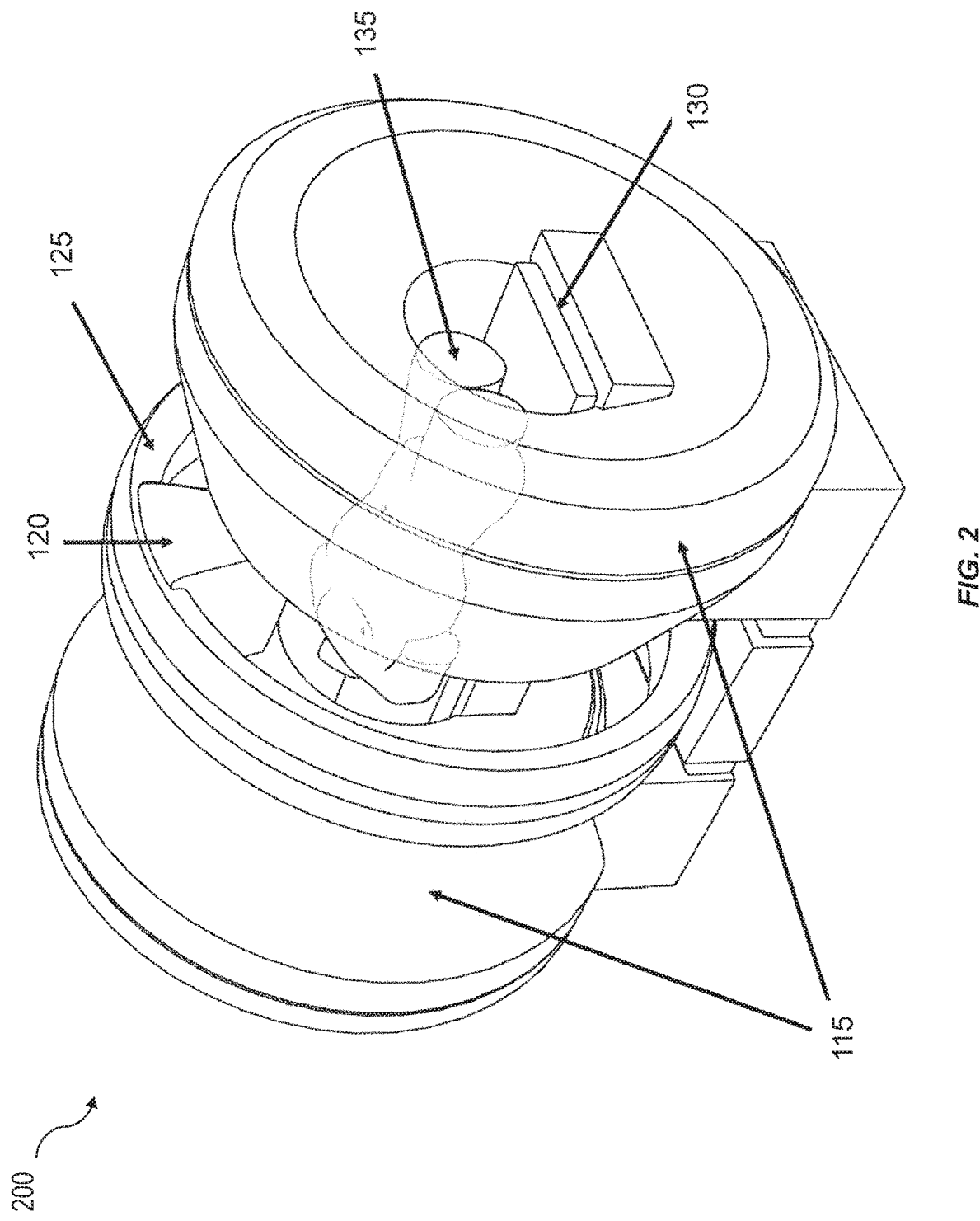
FIG. 2 shows a schematic diagram illustrating a demonstration of gantry rotation.
Figure 3:
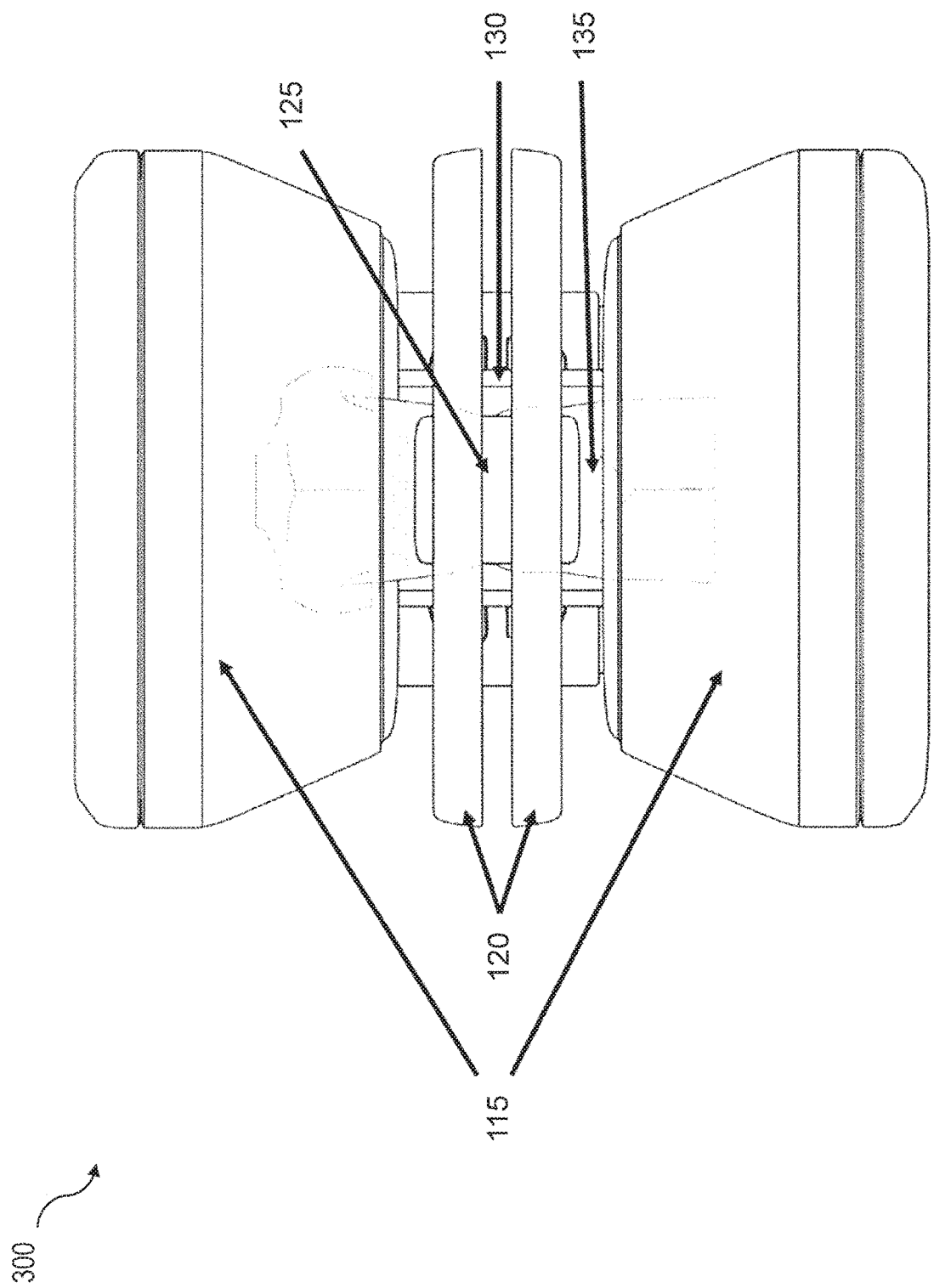
FIG. 3 shows a schematic diagram illustrating a top view of the system shown in FIG. 1.
Figure 4:
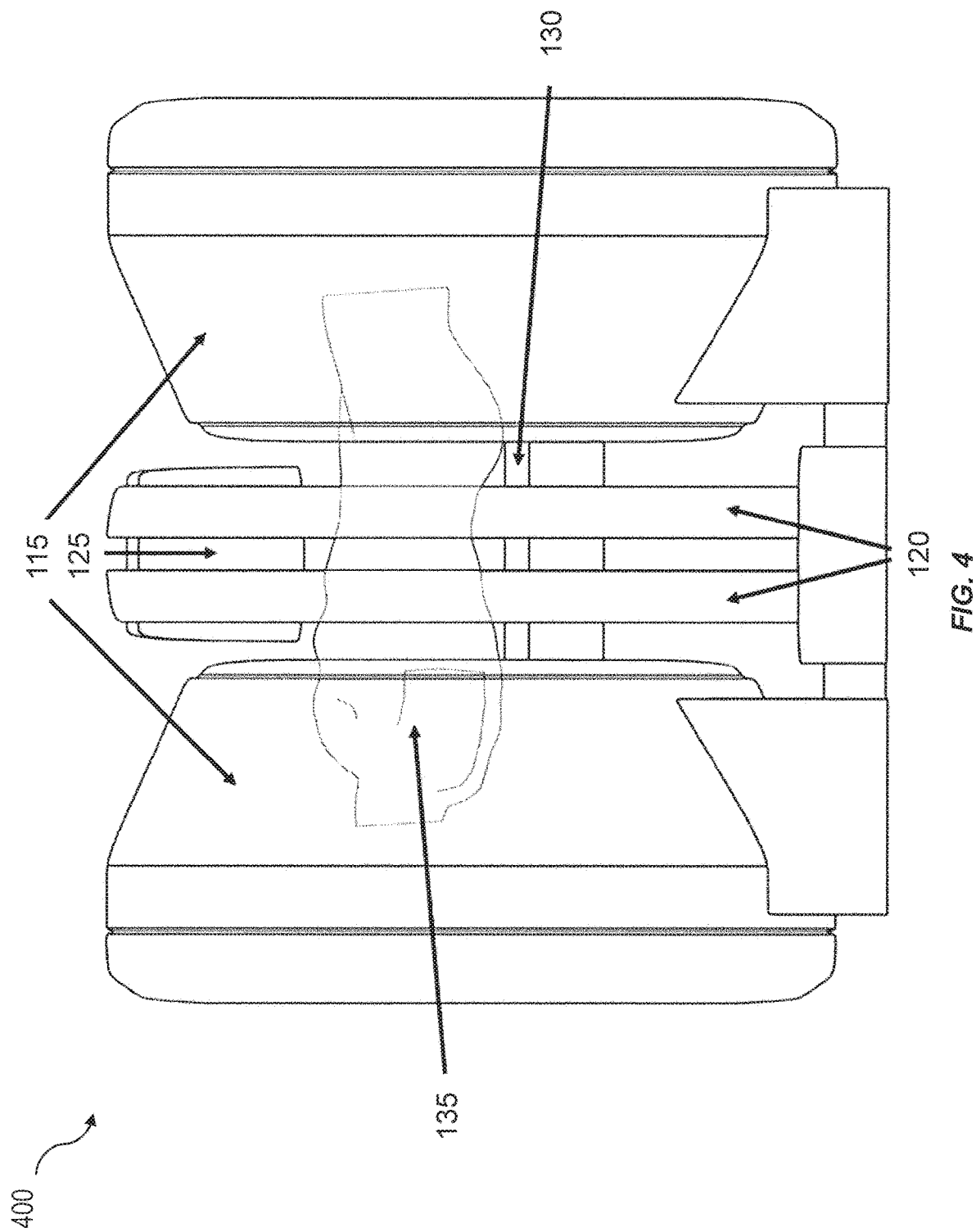
FIG. 4 shows a schematic diagram illustrating a side view of the system shown in FIG. 1.

Physiological changes that occur in tissues due to ionizing radiation create changes that can be detected with magnetic resonance imaging (MRI) as changes in anatomic morphology and signal intensity. In the prior, diagnostic art of MRI, these changes are generally considered to be impediments to further diagnosis and follow up and are described to avoid misinterpretation in a MRI diagnostic study. As an example, see "MRI appearance of radiation-induced changes of normal cervical tissues," Nömayr A, Lell M, Sweeney R, Bautz W, Lukas P. Eur Radiol. 2001; 11(9):1807-17.

In contrast, implementations of the current subject matter treat these changes are not merely impediments to proper radiologic diagnosis, but rather as useful tools in the assessment and improvement of radiation treatment techniques.

In currently available approaches, assessments of the probability that a disease under radiation treatment will be eradicated by radiotherapy or that a side effect will occur typically involves evaluating dose-volume information derived from a patient treatment plan. Changes in patient geometry and anatomy can cause the delivered dose to differ from the planned dose. As described in co-owned U.S. Pat. No. 7,907,987, improvements in radiation treatment can include accounting for the presence of patient motions and changes over the course of a radiation therapy delivery regime, for example by incorporating real-time simultaneous magnetic resonance imaging (MRI) into the radiation delivery process. The microenvironment of the tumor and healthy tissues being irradiated can also be influenced by the 4R's discussed above. However, effective and practical methods of in vivo assessment of such physiological reactions to radiotherapy have not previously existed.

The current subject matter includes approaches to acquiring, evaluating, and incorporating additional MRI data that can be obtained during a course of radiation therapy to improve a clinician's ability to assess the probability that the disease under radiation treatment will be eradicated or that a side effect will occur in a given patient that is undergoing radiation therapy. The assessment can be based at least in part on the measurement of physiological and morphological changes in the patient's tissues in response to the delivered radiation. This information can then be incorporated into the medical management and treatment of the patient to improve therapy outcomes and to mitigate side effects.

The amount of radiation used in photon radiation therapy is measured in gray (Gee), and varies depending on the type and stage of cancer being treated. For curative cases, the typical dose for a solid epithelial tumor ranges from 60 to 80 Gee, while lymphomas are treated with 20 to 40 Gee. Preventative (adjuvant) doses are typically around 45 to 60 Gy in fractions of 1.8 to 2 Gy (e.g., for breast, head, and neck cancers). Radiation oncologists may consider other factors when selecting a dose, including whether the patient is receiving chemotherapy, patient comorbidities, whether radiation therapy is being administered before or after surgery, and the degree of success of surgery.

Delivery parameters of a prescribed dose are determined during treatment planning (e.g. as part of a dosimetry analysis or other process). Treatment planning is generally performed on dedicated computers using specialized treatment planning software. Depending on the radiation delivery method, several angles or sources may be used to sum to the total necessary dose. A treatment planner generally seeks to design a plan that delivers a uniform prescription dose to the tumor and minimizes dose delivered to surrounding healthy tissues. The likelihood of controlling or curing the disease and the probability of side effect is determined by evaluating dose and dose-volume criteria that have been established through clinical experience and clinical trials.

The total dose delivered for a course of radiation therapy may be delivered in a single dose or fractionated (spread out over time). Fractionation allows normal cells time to recover, while tumor cells are generally less efficient in repair between fractions. Fractionation also allows tumor cells that were in a relatively radiation-resistant phase of the cell cycle during one treatment fraction to cycle into a sensitive phase of the cycle before the next treatment fraction is delivered. Similarly, tumor cells that were chronically or acutely hypoxic (and therefore more radiation-resistant) may re-oxygenate between fractions, improving the tumor cell kill. Fractionation regimens are individualized between different radiation therapy centers and even between individual doctors. The typical fractionation schedule for adults is 1.8 to 2 Gy per day, five days a week. In some cancer types, prolongation of the fraction schedule over too long can allow for the tumor to begin repopulating, and for these tumor types, including head-and-neck and cervical squamous cell cancers, radiation treatment is preferably completed within a certain amount of time. For children, a typical fraction size may be approximately 1.5 to 1.8 Gy per day, as smaller fraction sizes are associated with reduced incidence and severity of late effects in normal tissues.

In some cases, two fractions per day are used near the end of a course of treatment. This schedule, known as a concomitant boost regimen or hyperfractionation, is used on tumors that regenerate more quickly when they are smaller. In particular, tumors in the head- and-neck demonstrate this behavior.

Recently hypofractionation has become more common. This is a radiation treatment in which the total dose of radiation is divided into large doses, and treatments are given less than once a day. Typical doses vary significantly by cancer type, from approximately 3Gy per fraction to approximately 20Gy per fraction. A hypofractionation approach generally attempts to lessen the possibility of the cancer returning by not giving the cells enough time to reproduce. For single dose delivery or hypofractionation extra care is often taking in localizing and immobilizing the patient often with methods of stereotaxis.

With brachytherapy, implants can be continuously fractionated over minutes or hours, or they can be permanent seeds, which slowly deliver radiation continuously until they become inactive.

Magnetic resonance imagmg can be used to assess inflammatory and other responses in human tissues and tumors to provide a better measure of cell damage and tissue response than the physical dose distribution. Differences in radiosensitivity that may exist in the tumor or organ microenvironment or genetically from patient to patient will be accounted for with such a method. Many types of MRI scans can assess inflammatory response and morphological changes induced by ionizing radiation. Examples of MRI scans include basic MRI scans (e.g., $T_1$-weighted MRI, $T_2$-weighted MRI, $T^*_2$-weighted MRI, Spin density weighted MRI, and the like) and specialized MRI scans (e.g., diffusion MRI, magnetization transfer MRI, Tip MRI, Fluid attenuated inversion recovery, magnetic resonance angiography, magnetic resonance gated intracranial CSF dynamics; magnetic resonance spectroscopy, magnetic resonance spectroscopic imaging, functional MRI, and the like).

$T_1$-weighted scans refer to a set of standard scans that depict differences in the spin-lattice (or $T_1$) relaxation time of various tissues within the body. $T_1$-weighted images can be acquired using either spin echo or gradient-echo sequences. $T_1$-weighted contrast can be increased with the application of an inversion recovery RF pulse. Gradient-echo based $T_1$-weighted sequences can be acquired very rapidly because of their ability to use short inter-pulse repetition times (TR). $T_1$-weighted sequences are often collected before and after infusion of $T_1$-shortening MRI contrast agents. In the brain $T_1$-weighted scans provide appreciable contrast between gray and white matter. In the body, $T_1$-weighted scans work well for differentiating fat from water, with water appearing darker and fat brighter.

$T_2$-weighted scans refer to a set of standard scans that depict differences in the spin-spin (or $T_2$) relaxation time of various tissues within the body. Like the $T_1$-weighted scan, fat is differentiated from water. However, in $T_2$-weighted scans fat shows darker, and water lighter. For example, in the case of cerebral and spinal study, the CSF (cerebrospinal fluid) will be lighter in $T_2$-weighted images. These scans are therefore particularly well suited to imaging edema, with long echo times (TE) and long TR. Because the spin echo sequence is less susceptible to inhomogeneities in the magnetic field, these images have long been a clinical workhorse.

$T^*_2$ (pronounced "T 2 star") weighted scans use a gradient echo (GRE) sequence, with long TE and long TR. The GRE sequence used does not have the extra refocusing pulse used in spin echo so it is subject to additional losses above the normal $T_2$ decay (referred to as $T_2'$). These additional losses tend to make $T^*_2$ more prone to susceptibility losses at air-tissue boundaries, but can increase contrast for certain types of tissue, such as venous blood.

Spin density, which is also referred to as proton density, weighted scans are generally intended to have no contrast from either $T_2$ or $T_1$ decay, with the only signal change coming from differences in the amount of available spins (hydrogen nuclei in water). This approach uses a spin echo or sometimes a gradient echo sequence, with short TE and long TR.

Diffusion MRI, a type of specialized MRI scan, measures the diffusion of water molecules m biological tissues. Clinically, diffusion MRI is useful for the diagnoses of conditions (e.g., stroke) or neurological disorders (e.g., Multiple Sclerosis), and helps improve understanding of the connectivity of white matter axons in the central nervous system. In an isotropic medium (inside a glass of water for example), water molecules naturally move randomly according to turbulence and Brownian motion. In biological tissues, however, where the Reynolds number is low enough for flows to be laminar, the diffusion may be anisotropic. For example, a molecule inside the axon of a neuron has a low probability of crossing the myelin membrane. Therefore the molecule moves principally along the axis of the neural fiber. If it is known that molecules in a particular voxel diffuse principally in one direction, the assumption can be made that the majority of the fibers in this area are going parallel to that direction.

The recent development of diffusion tensor imaging (DTI) enables diffusion to be measured in multiple directions and the fractional anisotropy in each direction to be calculated for each voxel. This development can enable researchers to make brain maps of fiber directions to examine the connectivity of different regions in the brain (using tractography) or to examine areas of neural degeneration and demyelination in diseases like multiple sclerosis.

Another application of diffusion MRI is diffusion-weighted imaging (DWI). Following an ischemic stroke, DWI is highly sensitive to the changes occurring in the lesion. It is speculated that increases in restriction (barriers) to water diffusion, as a result of cytotoxic edema (cellular swelling), can be responsible for the increase in signal on a DWI scan. The DWI enhancement appears within 5-10 minutes of the onset of stroke symptoms (as compared with computed tomography, which often does not detect changes of acute infarct for up to 4-6 hours) and remains for up to two weeks. Coupled with imaging of cerebral perfusion, researchers can highlight regions of "perfusion/diffusion mismatch" that may indicate regions capable of salvage by reperfusion therapy.

Like many other specialized applications, this technique is usually coupled with a fast image acquisition sequence, such as echo planar imaging sequence.

Magnetization transfer (MT) refers to the transfer of longitudinal magnetization from free water protons to hydration water protons in NMR and MRI. In magnetic resonance imaging of molecular solutions, such as protein solutions, two types of water molecules, free (bulk) and hydration (bound), are found. Free water protons have faster average rotational frequency and hence less fixed water molecules that may cause local field inhomogeneity. Because of this uniformity, most free water protons have a resonance frequency lying narrowly around the normal proton resonance frequency of 63 MHz (at 1.5 teslas). This also results in slower transverse magnetization dephasing and hence longer $T_2$. Conversely, hydration water molecules are slowed down by interaction with solute molecules and hence create field inhomogeneities that lead to wider resonance frequency spectrum.

In free liquids, protons, which may be viewed classically as small magnetic dipoles, exhibit translational and rotational motions. These moving dipoles disturb the surrounding magnetic field however on long enough time-scales (which may be nanoseconds) the average field caused by the motion of protons is zero. This effect is known as "motional averaging" or narrowing and is characteristic of protons moving freely in a liquid phase. On the other hand, protons bound to macromolecules, such as proteins, tend to have a fixed orientation and so the average magnetic field in close proximity to such structures does not average to zero. The result is a spatial pattern in the magnetic field that gives rise to a residual dipolar coupling (range of precession frequencies) for the protons experiencing the magnetic field. The wide frequency distribution appears as a broad spectrum that may be several kHz wide. The net signal from these protons disappears very quickly, in inverse proportion to the width, due to the loss of coherence of the spins, i.e. $T_2$ relaxation. Due to exchange mechanisms, such as spin transfer or proton chemical exchange, the (incoherent) spins bound to the macromolecules continually switch places with (coherent) spins in the bulk media and establish a dynamic equilibrium.

Although there is generally no measurable signal from the bound spins, or the bound spins that exchange into the bulk media, their longitudinal magnetization is preserved and may typically recover only via the relatively slow process of $T_1$ relaxation. If the longitudinal magnetization of just the bound spins can be altered, then the effect can be measured in the spins of the bulk media due to the exchange processes. A magnetization transfer sequence applies radiofrequency (RF) saturation at a frequency that is far off resonance for the narrow line of bulk water but still on resonance for the bound protons with a spectral linewidth on the order of kHz. The RF application causes saturation of the bound spins which exchange into the bulk water, resulting in a loss of longitudinal magnetization and hence signal decrease in the bulk water, thereby providing an indirect measure of macromolecular content in tissue. Implementation of magnetization transfer involves choosing suitable frequency offsets and pulse shapes to saturate the bound spins sufficiently strongly, within the safety limits of specific absorption rate for RF irradiation.

Tip MRI generally relies upon the fact that molecules have a kinetic energy that is a function of the temperature and is expressed as translational and rotational motions, and by collisions between molecules. The moving dipoles disturb the magnetic field but are often extremely rapid so that the average effect over a long time-scale may be zero. However, depending on the time-scale, the interactions between the dipoles do not always average away. At the slowest extreme the interaction time is effectively infinite and occurs where there are large, stationary field disturbances (e.g. a metallic implant). In this case the loss of coherence is described as a "static dephasing". $T^*_2$ is a measure of the loss of coherence in an ensemble of spins that include all interactions (including static dephasing). $T_2$ is a measure of the loss of coherence that excludes static dephasing, using an RF pulse to reverse the slowest types of dipolar interaction. There is in fact a continuum of interaction time-scales in a given biological sample and the properties of the refocusing RF pulse can be tuned to refocus more than just static dephasing. In general, the rate of decay of an ensemble of spins is a function of the interaction times and also the power of the RF pulse. Measurement of spin-lattice relaxation time in the rotating frame occurring under the influence of RF, is known as $T_1\rho$. It is similar to $T_2$ decay but with some slower dipolar interactions refocused as well as the static interactions, hence $T_1\rho \geq T_2$.

Fluid attenuated inversion recovery (FLAIR) is an inversion-recovery pulse sequence used to null signal from fluids. For example, it can be used in brain imaging to suppress cerebrospinal fluid (CSF) so as to bring out the periventricular hyperintense lesions, such as multiple sclerosis (MS) plaques. By carefully choosing the inversion time $T_1$ (the time between the inversion and excitation pulses), the signal from any particular tissue can be suppressed.

Magnetic resonance angiography (MRA) generates pictures of the arteries to evaluate them for stenosis (abnormal narrowing) or aneurysms (vessel wall dilatations, at risk of rupture). MRA is often used to evaluate the arteries of the neck and brain, the thoracic and abdominal aorta, the renal arteries, and the legs (called a "run-off"). A variety of techniques can be used to generate the pictures, such as administration of a paramagnetic contrast agent (gadolinium) or using a technique known as "flow-related enhancement" (e.g. 2D and 3D time-of-flight sequences), where most of the signal on an image is due to blood that recently moved into that plane. Fast low angle shot (FLASH) MRI is a related technique. Techniques involving phase accumulation (known as phase contrast angiography) can also be used to generate flow velocity maps easily and accurately. Magnetic resonance venography (MRV) is a similar procedure that is used to image veins. In this method, the tissue is now excited inferiorly, while signal is gathered in the plane immediately superior to the excitation plane-thus imaging the venous blood that recently moved from the excited plane.

A magnetic resonance gated intracranial cerebrospinal fluid (CSF) or liquor dynamics (MR-GILD) technique is an MR sequence based on bipolar gradient pulse used to demonstrate CSF pulsatile flow in ventricles, cisterns, aqueduct of Sylvius and entire intracranial CSF pathway. It is a method for analyzing CSF circulatory system dynamics in patients with CSF obstructive lesions such as normal pressure hydrocephalus. It also allows visualization of both arterial and venous pulsatile blood flow in vessels without use of contrast agents.

Magnetic resonance spectroscopy (MRS) can be used to measure the levels of different metabolites in body tissues. The MR signal produces a spectrum of resonances that correspond to different molecular arrangements of the isotope being "excited." This signature can be used to diagnose certain metabolic disorders, especially those affecting the brain, and to provide information on tumor metabolism. Magnetic resonance spectroscopic imaging (MRSI) combines both spectroscopic and imaging methods to produce spatially localized spectra from within the sample or patient.

The spatial resolution is much lower (limited by the available SNR), but the spectra in each voxel contains information about many metabolites. Because the available signal is used to encode spatial and spectral information, MRSI requires high SNR achievable only at higher field strengths (3 T and above).

Functional MRI (fMRI) measures signal changes in the brain that are due to changing neural activity. The brain is scanned at low resolution but at a rapid rate (typically once every 2-3 seconds). Increases in neural activity cause changes in the MR signal via $T^*_2$ changes. This mechanism is referred to as the blood-oxygen-level dependent (BOLD) effect. Increased neural activity causes an increased demand for oxygen, and the vascular system actually overcompensates for this, increasing the amount of oxygenated hemoglobin relative to deoxygenated hemoglobin. Because deoxygenated hemoglobin attenuates the MR signal, the vascular response leads to a signal increase that is related to the neural activity. The precise nature of the relationship between neural activity and the BOLD signal is a subject of current research. The BOLD effect also allows for the generation of high resolution 3D maps of the venous vasculature within neural tissue.

While a BOLD signal is the most common method employed for neuroscience studies in human subjects, the flexible nature of MR imaging provides means to sensitize the signal to other aspects of the blood supply. Alternative techniques employ arterial spin labeling (ASL) or weight the MRI signal by cerebral blood flow (CBF) and cerebral blood volume (CBV). The CBV method requires injection of a class of MRI contrast agents that are now in human clinical trials. Because this method has been shown to be far more sensitive than the BOLD technique in preclinical studies, it may potentially expand the role of fMRI in clinical applications. The CBF method provides more quantitative information than the BOLD signal, albeit at a significant loss of detection sensitivity.

The acute and late responses of human tissues to ionizing radiation can be imaged with MRI techniques during treatment to assess the true radiosensitivity modified response of tissue and tumor to the delivered ionizing radiation. For example, epithelial surfaces may sustain damage from radiation therapy and internal surfaces may thicken which can be detected and measured with $T_1$, $T_2$, $T^*_2$, or spin density imaging. In other examples, imaging can detect irradiated tissues that tend to become less elastic over time due to a diffuse scarring process. Fibrotic response can be imaged, as well as Lymphedema, which is a condition of localized fluid retention and tissue swelling resulting from damage to the lymphatic system sustained during radiation therapy. Lymphedema is the most commonly reported complication in breast radiation therapy patients who receive adjuvant axillary radiotherapy following surgery to clear the axillary lymph nodes).

Edema is part of the general inflammation that occurs from radiation damage of cells, as further explained below, and can be directly measured with $T_1$ and $T_2$ weighted MRI consistent with implementations of the current subject matter which includes techniques, methods, systems, apparatus, articles, etc. relating to tracking of radiation damage via inflammatory response expressed as edema. Quantitative measurements of inflammation response can result from measures the swelling due to acute inflammation inside a patient's tissue with MRI radiography.

Inflammation is part of the complex biological response of vascular tissues to harmful stimuli, such as ionizing radiation. Other stimuli such as cancerous tumor invasion, pathogens, damaged cells or irritants can also cause inflammation, but baseline measurements and assessment can be separated from ionizing radiation induced inflammation. Inflammation is a protective attempt by the organism to remove the injurious stimuli, dead cells or matter and to initiate the healing process. Inflammation is considered as a mechanism of innate immunity or sensitivity to the stimulus causing it. It is also an important mechanism for the healing of wounds and infections. However, chronic inflammation can also lead to a host of diseases, such as hay fever, periodontitis, atherosclerosis, rheumatoid arthritis, and even cancer (e.g., gallbladder carcinoma). Therefore, inflammation is closely regulated by the body.

Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process.

The classic signs and symptoms of acute inflammation are redness, swelling, heat, pain, and loss of tissue function. Any sign may be observed in specific instances, but no single sign must, as a matter of course, be present. Typically inflammation is observed visually and qualitatively by external examination by a medical practitioner. The classic signs appear when acute inflammation occurs on a body's surface, whereas acute inflammation of internal organs may not result in the full set. Pain generally results only where the appropriate sensory nerve endings exist in the inflamed area. For example, acute inflammation of the lung (pneumonia) does not cause pain unless the inflammation involves the parietal pleura, which does have pain-sensitive nerve endings.

Acute inflammation is a short-term process, usually appearing within a few minutes or hours and ceasing upon the removal of the injurious stimulus. Redness and heat are due to increased blood flow at body core temperature to the inflamed site, swelling is caused by accumulation of fluid, and pain is due to release of chemicals that stimulate nerve endings. Loss of function can have multiple causes.

Cells present in all tissues, such as for example resident macrophages, dendritic cells, histiocytes, Kupffer cells, mastocytes, etc. typically initiate the process of acute inflammation. These cells present on their surfaces certain receptors named pattern recognition receptors (PRRs), which recognize molecules that are broadly shared by pathogens but distinguishable from host molecules, collectively referred to as pathogen-associated molecular patterns (PAMPs). At the onset of an infection, burn, or other injuries, these cells undergo activation (i.e., one of their PRRs recognize a PAMP) and release inflammatory mediators responsible for the clinical signs of inflammation. Vasodilation and its resulting increased blood flow causes the redness (rubor) and increased heat (calor). Increased permeability of the blood vessels results in an exudation (leakage) of plasma proteins and fluid into the tissue (edema), which manifests itself as swelling (tumor). Some of the released mediators such as bradykinin increase the sensitivity to pain (hyperalgesia, dolor). The mediator molecules also alter the blood vessels to permit the migration of leukocytes, mainly neutrophils, outside of the blood vessels (extravasation) into the tissue. The neutrophils migrate along a chemotactic gradient created by the local cells to reach the site of injury. The loss of function (functio laesa) is probably the result of a neurological reflex in response to pain.

In addition to cell-derived mediators, several acellular biochemical cascade systems consisting of preformed plasma proteins act in parallel to initiate and propagate the inflammatory response. These include the complement system activated by bacteria, and the coagulation and fibrinolysis systems activated by necrosis, e.g. a burn or a trauma.

The acute inflammatory response requires constant stimulation to be sustained. Inflammatory mediators have short half lives and are quickly degraded in the tissue. Hence, acute inflammation generally ceases and diminishes once the stimulus has been removed.

The exudative component involves the movement of plasma fluid, containing important proteins such as fibrin and immunoglobulins (antibodies), into inflamed tissue. This movement is achieved via the chemically induced dilation and increased permeability of blood vessels, which results in a net loss of blood plasma. The increased collection of fluid into the tissue causes it to swell (edema). This extravasated fluid is funneled by lymphatics to the regional lymph nodes, flushing bacteria along to start the recognition and attack phase of the adaptive immune system.

Acute inflammation is characterized by marked vascular changes, including but not necessarily limited to vasodilation, increased permeability, and increased blood flow, which are induced by the actions of various inflammatory mediators. Vasodilation occurs first at the arteriole level, progressing to the capillary level, and can bring about a net increase in the amount of blood present, which can in turn cause the redness and heat of inflammation. Increased permeability of the vessels results in the movement of plasma into the tissues, with resultant stasis due to the increase in the concentration of the cells within blood. Enlarged vessels packed with cells typically characterize this condition. Stasis allows leukocytes to marginate (move) along the endothelium, a process critical to their recruitment into the tissues. Normal flowing blood prevents this, as the shearing force along the periphery of the vessels moves cells in the blood into the middle of the vessel.

Inflammation orchestrates the microenvironment around tumors, which can contribute to proliferation, survival and migration. Cancer cells use selectins, chemokines and their receptors for invasion, migration, metastasis, and the like. On the other hand, many cells of the immune system contribute to cancer immunology, suppressing cancer. Molecular intersection between receptors of steroid hormones, which have important effects on cellular development, and transcription factors that play key roles in inflammation, such as NF-KB, may mediate some of the most critical effects of inflammatory stimuli on cancer cells. This capacity of a mediator of inflammation to influence the effects of steroid hormones in cells is very likely to affect carcinogenesis in some examples. On the other hand, due to the modular nature of many steroid hormone receptors, this interaction may offer ways to interfere with cancer progression, for example through targeting of a specific protein domain in a specific cell type. Such an approach may limit side effects that are unrelated to the tumor of interest, and may help preserve vital homeostatic functions and developmental processes in the organism.

The outcome in a particular circumstance will be determined by the tissue in which the injury has occurred and the injurious agent that is causing it. Possible outcomes to inflammation can include resolution, fibrosis, abcess formation, chronic inflammation, swelling, and the like.

Resolution is the complete restoration of the inflamed tissue back to a normal status. Inflammatory measures such as vasodilation, chemical production, and leukocyte infiltration cease, and damaged parenchymal cells regenerate. In situations where limited or short lived inflammation has occurred this is usually the outcome.

Large amounts of tissue destruction, or damage in tissues unable to regenerate, may not be completely regenerated by the body. Fibrosis refers to fibrous scarring which occurs in these areas of damage to form a scar composed primarily of collagen. The scar will not contain any specialized structures, such as parenchymal cells. Accordingly, functional impairment may occur.

Abscess formation includes formation of a cavity containing pus, which is an opaque liquid containing dead white blood cells and bacteria with general debris from destroyed cells.

If an injurious agent causing acute inflammation persists, chronic inflammation will ensue. This process, marked by inflammation lasting many days, months or even years, may lead to the formation of a chronic wound. Chronic inflammation is characterized by the dominating presence of macrophages in the injured tissue. These cells are powerful defensive agents of the body, but the toxins they release (including reactive oxygen species) are injurious to the organism's own tissues as well as invading agents. Consequently, chronic inflammation is almost always accompanied by tissue destruction.

In medical parlance, swelling, turgescence, or tumefaction is a transient abnormal enlargement of a body part or area not caused by proliferation of cells. It is caused by accumulation of fluid in tissues. It can occur throughout the body (generalized), or a specific part or organ can be affected (localized). Swelling is considered one of the five characteristics of inflammation along with pain, heat, redness, and loss of function. A body part may swell in response to injury, infection, or disease. Swelling can occur if the body is not circulating fluid well.

Generalized swelling, or massive edema (also called anasarca) is a common sign in severely ill people. Although slight edema may be difficult to detect to the untrained eye, especially in an overweight person, massive edema is generally very obvious. Edema (American English) or oedema (British English), formerly known as dropsy or hydropsy, is an abnormal accumulation of fluid beneath the skin or in one or more cavities of the body that produces swelling. Generally, the amount of interstitial fluid is determined by the balance of fluid homeostasis, and increased secretion of fluid into the interstitium or impaired removal of this fluid may cause edema.

Cutaneous edema is referred to as "pitting" when, after pressure is applied to a small area, the indentation persists for some time after the release of the pressure. Peripheral pitting edema is the more common type, resulting from water retention and can be caused by systemic diseases, pregnancy in some women, either directly or as a result of heart failure, or local conditions such as varicose veins, thrombophlebitis, insect bites, and dermatitis. Non-pitting edema is observed when the indentation does not persist. It is associated with such conditions as lymphedema, lipedema and myxedema.

Causes of edema which are generalized to the whole body can cause edema in multiple organs and peripherally. For example, severe heart failure can cause pulmonary edema, pleural effusions, ascites and peripheral edema.

Although a low plasma oncotic pressure is widely cited for the edema of nephrotic syndrome, most physicians note that the edema may occur before there is any significant protein in the urine (proteinuria) or fall in plasma protein level. Fortunately there is another explanation available. Most forms of nephrotic syndrome are due to biochemical and structural changes in the basement membrane of capillaries in the kidney glomeruli, and these changes occur, if to a lesser degree, in the vessels of most other tissues of the body. Thus the resulting increase in permeability that leads to protein in the urine can explain the edema if all other vessels are more permeable as well.

As well as the previously mentioned conditions, edemas often occur during the late stages of pregnancy in some women. This is more common with those of a history of pulmonary problems or poor circulation also being intensified if arthritis is already present in that particular woman. Women that already have arthritic problems most often have to seek medical help for pain caused from over-reactive swelling. Edemas that occur during pregnancy are usually found in the lower part of the leg, usually from the calf down.

An edema can occur in specific organs as part of inflammations, tendinitis, or pancreatitis, for example. Certain organs develop edema through tissue specific mechanisms. For example, cerebral edema is extracellular fluid accumulation in the brain. It can occur in toxic or abnormal metabolic states and conditions such as systemic lupus or reduced oxygen at high altitudes. It causes drowsiness or loss of consciousness. Pulmonary edema occurs when the pressure in blood vessels in the lung is raised because of obstruction to remove blood via the pulmonary veins. This is usually due to failure of the left ventricle of the heart. It can also occur in altitude sickness or on inhalation of toxic chemicals. Pulmonary edema produces shortness of breath. Pleural effusions may occur when fluid also accumulates in the pleural cavity. Edema may also be found in the cornea of the eye with glaucoma, severe conjunctivitis or keratitis or after surgery. Such edemas may result in the patient seeing colored haloes around bright lights. Edema surrounding the eyes is called periorbital edema or eye puffiness. The periorbital tissues are most noticeably swollen immediately after waking, perhaps as a result of the gravitational redistribution of fluid in the horizontal position.

Common appearances of cutaneous edema are observed with mosquito bites, spider bites, bee stings (wheal and flare), and skin contact with certain plants such as Poison Ivy or Western Poison Oak, the latter of which are termed contact dermatitis. Another cutaneous form of edema is myxedema, which is caused by increased deposition of connective tissue. In myxedema (and a variety of other rarer conditions) edema is caused by an increased tendency of the tissue to hold water within its extracellular space. In myxedema this is because of an increase in hydrophilic carbohydrate-rich molecules (perhaps mostly hyaluronan) deposited in the tissue matrix. Edema forms more easily in dependent areas in the elderly (sitting in chairs at home or on airplanes) and this is not well understood. Estrogens alter body weight in part through changes in tissue water content. There may be a variety of poorly understood situations in which transfer of water from tissue matrix to lymphatics is impaired because of changes in the hydrophilicity of the tissue or failure of the "wicking" function of terminal lymphatic capillaries.

In lymphedema, abnormal removal of interstitial fluid is caused by failure of the lymphatic system. This may be due to obstruction from, for example, pressure from a cancer or enlarged lymph nodes, destruction of lymph vessels by radiotherapy, or infiltration of the lymphatics by infection (such as elephantiasis). It is most commonly due to a failure of the pumping action of muscles due to immobility, most strikingly in conditions such as multiple sclerosis, or paraplegia. Lymphatic return of fluid is also dependent on a pumping action of structures known as lymph hearts. It has been suggested that the edema that occurs in some people following use of aspirin-like cyclo-oxygenase inhibitors such as ibuprofen or indomethacin may be due to inhibition of lymph heart action.

Factors that can contribute to the formation of edema include increased hydrostatic pressure, reduced oncotic pressure within blood vessels, increased tissue oncotic pressure, increased blood vessel wall permeability (e.g., inflammation), obstruction of fluid clearance via the lymphatic system, and changes in the water retaining properties of the tissues themselves. Raised hydrostatic pressure often reflects retention of water and sodium by the kidney.

Generation of interstitial fluid is regulated by the forces of the Starling equation, which can be represented by the is the net fluid movement between compartments Jv as follows:

$$J_v = K_f F_D \tag{1}$$

where $K_f$ is the filtration coefficient (a proportionality constant), and the net driving force $F_D$ can be represented as $$F_D = [P_c - P_i] - \sigma[\pi_c - \pi_i] \tag{2}$$

where Pc is the capillary hydrostatic pressure, $P_i$ is the interstitial hydrostatic pressure, $\pi_c$ is the capillary oncotic pressure, $\pi_i$ is the interstitial oncotic pressure, and $\sigma$ is the reflection coefficient.

Hydrostatic pressure within blood vessels tends to cause water to filter out into the tissue. This leads to a difference in protein concentration between blood plasma and tissue. As a result, the oncotic pressure of the higher level of protein in the plasma tends to draw water back into the blood vessels from the tissue. Starling's equation states that the rate of leakage of fluid is determined by the difference between the two forces and also by the permeability of the vessel wall to water, which determines the rate of flow for a given force imbalance. Most water leakage occurs in capillaries or post capillary venules, which have a semi-permeable membrane wall that allows water to pass more freely than protein. The protein is said to be reflected and the efficiency of reflection is given by a reflection constant of up to 1. If the gaps between the cells of the vessel wall open up then permeability to water is increased first, but as the gaps increase in size, permeability to protein also increases with a fall in reflection coefficient.

Changes in values of the variables in Starling's equation can contribute to the formation of edemas either by an increase in hydrostatic pressure within the blood vessel, a decrease in the oncotic pressure within the blood vessel or an increase in vessel wall permeability. The latter has two effects. It allows water to flow more freely and it reduces the oncotic pressure difference by allowing protein to leave the vessel more easily.

The Dose-volume histogram (DVH) us a concept used in radiation treatment planning. DVHs were introduced by Michael Goitein, who also introduced radiation therapy concepts such as the "beam's-eye-view," "digitally reconstructed radiograph," and uncertainty/error in planning and positioning, among others, and Verhey in 1979 in a publication by Shipley et al. A DVH summarizes 3D dose distributions in a graphical 2D format. In modem radiation therapy, 3D dose distributions are typically created in a computerized treatment planning system based on a 3D reconstruction of a CT or MR scan. The "volume" referred to in DVH analysis can be a target of radiation treatment, a healthy organ nearby a target, or an arbitrary structure.

DVHs can be visualized in either of two ways: differential DVHs or cumulative DVHs. A DVH is created by first determining the size of the dose bins of the histogram. Bins can be of arbitrary size, for example, 0 to 1 Gy, 1.001 to 2 Gy, 2.001 to 3 Gy, etc. In a differential DVH, bar or column height indicates the volume of structure receiving a dose given by the bin. Bin doses are along the horizontal axis, and structure volumes (either percent or absolute volumes) are on the vertical.

The differential DVH takes the appearance of a typical histogram. The cumulative DVH is plotted with bin doses along the horizontal axis, as well. However, the column height of the first bin (for example, 0 to 1 Gy) represents the volume of structure receiving greater than or equal to that dose. The column height of the second bin (for example, 1.001-2 Gy) represents the volume of structure receiving greater than or equal to that dose, etc. With very fine (small) bin sizes, the cumulative DVH takes on the appearance of a smooth line graph. The lines always slope and start from top-left to bottom-right. For a structure receiving a very homogenous dose, for example, 100% of the volume receiving exactly 10 Gy, the cumulative DVH will appear as a horizontal line at the top of the graph, at 100% volume as plotted vertically, with a vertical drop at 10 Gy on the horizontal axis.

Cumulative DVHs are overwhelmingly used and preferred over differential DVHs. The DVH is ubiquitous in the medical specialty of radiation oncology. A DVH used clinically usually includes all structures and targets of interest in the radiotherapy plan, with each line plotted in a different color representing a different structure. The vertical axis is almost always plotted as percent volume (rather than absolute volume), as well. Clinical studies commonly employ DVH metrics to correlate with patient toxicities and outcomes.

A drawback of the DVH methodology is that it offers no spatial information. In other words, a DVH does not show where within a structure a dose is received. Also, DVHs from initial radiotherapy plans represent the doses relative to structures at the start of radiation treatment. As treatment progresses and time elapses, if there are changes (i.e. if patients lose weight, if tumors shrink, if organs change shape, etc.), the original DVH loses validity, for example due to a change in the denominator for one or more of the calculations inherent in the presented data. The spatial attributes of a dose distribution can be visualized by scrolling through orthogonal images with overlain dose distributions.

The current practice of radiation oncology correlates the probability of controlling or curing a tumor and the probability of inducing a deadly or debilitating side effect in a healthy or functional organ with data derived from a dose volume histogram and point, planar, or volumetric or dose distributions computed from a radiation therapy treatment plan.

Ionizing radiation dose is the energy per unit mass of ionizing radiation delivered to a patient or object. It is intended to be a quantitative measure of the amount of damage caused by the radiation to the DNA or other critical molecules of cancerous or targeted cells, and unavoidable irradiated healthy or functional cells. However, the 4 R's of radiobiology which are known to vary in different individuals due to genetic, morphologic, and pathologic reasons can greatly influence the actual damage caused by the radiation to the DNA or other critical molecules of cancerous or targeted cells, and unavoidably irradiated healthy or functional cells.

When cells are irradiated and damaged or killed by ionizing radiation, this stimulus induces an inflammation response in the irradiated tissues. Because this response is mediated by actual damage to the cells and tissues, it is a more direct measure of actual damage and cell death than delivered physical ionizing radiation dose.

The inflammation response can be measured as acute edema produced following or during radiation delivery. The change in MR imaging signal of tissues before and after the application of ionizing radiation is a direct quantitative measure of the increase in fluid, seen as a decrease in T1 weighted MR scans and a corresponding increase in $T_2$ (or $T^*_2$) weighted MR scans of the same anatomy in the same patient. This decrease in $T_1$, increase in $T_2$, or both, is a direct quantitative measure of the inflammation. The time from delivery of stimulus and the length of the scan can also be accounted for in the measure to allow for the buildup or decay of induced edema. This signal intensity can then be represented as an inflammation distribution to replace the dose distribution for evaluation of delivered cellular damage. Similarly, inflammation volume histograms can be produced and correlated to patient outcomes and toxicity. Such tools provide a better predictor of probability of tumor control or cure as well as probability of normal or healthy tissue toxicity as the inflammation, as measured by induced edema, is in direct response to the ionizing radiation stimulus.

In further implementations of the current subject matter, observation of inflammation outside of regions intended to receive damage from ionizing radiation can be used as a safety feature to alert clinical users to unintended or accidental delivery of ionizing radiation.

Inflammation response changes the fluid content of the tissue receiving radiation damage. This increase in fluid changes the material in the beam path such that the effective atomic number is different and positions at which different types of radiation are absorbed can also change. For example, an increase in fluid content can result in less "fat-like" material (e.g. $CH_2$) and more "water-like" material in the beam path. In proton therapy or heavy ion therapy, stopping powers for the delivered beam constituents can thereby be changed at a local level, thereby changing the range of the Bragg peak and thus changing the delivered dose distribution. Likewise, an increase in hydrogen content can change the dose from a neutron beam. Thus, quantitative assessment of edema with MRI scans can be used to improve the ability to compute dose for proton, heavy ion, and neutron therapy as well.

Implementations of the current subject matter can be realized using a system or other apparatus capable of capturing MRI images of at least part of a patient with at least some degree of concurrency with delivery of one or more radiation beams. In other words, one or more MRI images can be captured during delivery of a fraction of a radiation therapy dose. This technology can also be referred to as "intra-fraction" MRI. In other implementations of the current subject matter, MRI can be used periodically, optionally but not necessarily within radiation fractions, to collected differential data characterizing a change in edema in a patient during a course of treatment. For example, a baseline scan can be performed of an area being treated, and then one or more additional scans can be collected over the course of treatment to quantify changes in edema in the treated tissues and those tissues surrounding the treated tissue or otherwise affected by one or more radiation beams. The one or more additional scans can optionally include one or more of a scan or scans performed during at least one fraction, a scan or scans performed between two or more fractions in a series of fractions, a scan or scans performed at some other interval (which can be fixed or variable), and the like.

A non-limiting example of a system capable of intra-fraction MRI imaging is described in co-owned co-owned U.S. Pat. No. 7,907,987, the disclosure of which is incorporated herein by reference in its entirety. FIG. 1 through FIG. 5 show views 100, 200, 300, 400, 500, respectively, illustrating examples of features that can be included in such a system. A main magnet Helmholtz coil pair 115 of an MRI machine can be designed as a split solenoid so that a patient couch 130 runs through a cylindrical bore in the middle of the magnets and a radiation source 120 (e.g., a linear accelerator, a radioisotope source, etc. capable of delivering one or more of radioisotope beams, proton beams, heavy ion beams, neutron beams, X-rays, or the like) can be aimed down the gap between the two solenoidal sections 115 at a patient 135 on the patient couch 130. The split solenoidal MRI magnets 115 can remain stationary while the radiation source 120, which can include a multi-leaf collimator intensity modulated radiation therapy (IMRT) unit, is rotated axially around the couch on a gantry 125. More than one radiation source 120 can be beneficially employed. The patient 135 is positioned on the patient couch 130 for simultaneous (or at least approximately concurrent or at least approximately simultaneous) imaging and treatment.

Figure 5:
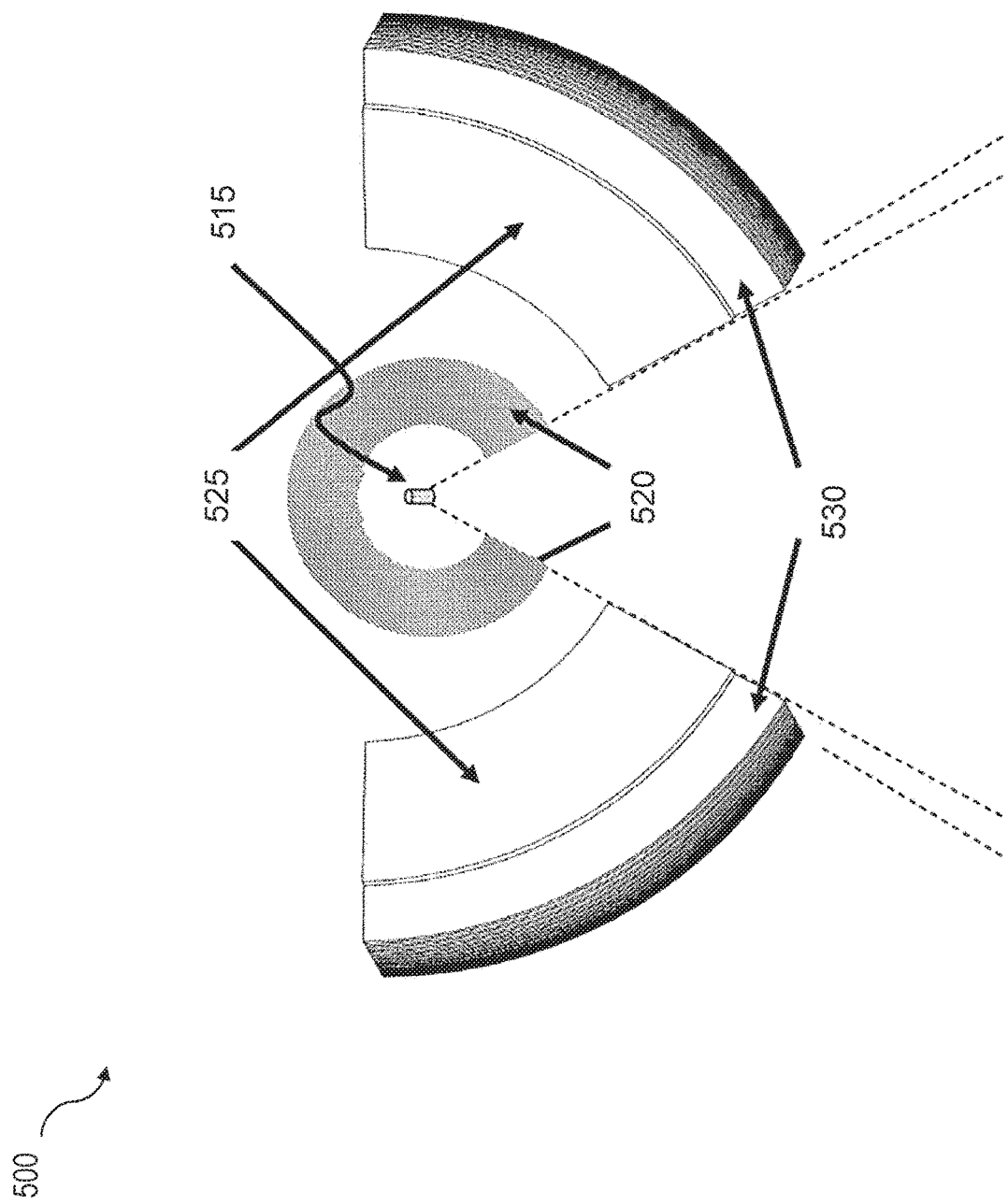
FIG. 5 shows a detailed schematic of a co-registered isotopic radiation source with a multi-leaf collimator, such as for example that shown in FIG. 1 through FIG. 4.

As shown in FIG. 5, the radiation source 120 with a multi-leaf collimator can contain a radioisotopic source 515 (or other radiation source) which can optionally be collimated with a fixed primary collimator 520, a secondary doubly divergent multileaf collimator 525, and tertiary multi-leaf collimator 530 to block interleaf leakage from the secondary multi-leaf collimator 525. It will be understood that other systems capable of producing MRI imagery either during a fraction or otherwise substantially concurrently with the fraction (e.g. within a short period of time before after, or during a fraction) can also be useful in implementing the current subject matter. Additionally, in implementations of the current subject matter in which intra-fraction MRI scans are used, conventional MRI systems that do not incorporate concurrent radiation delivery can also be used.

Figure 6:
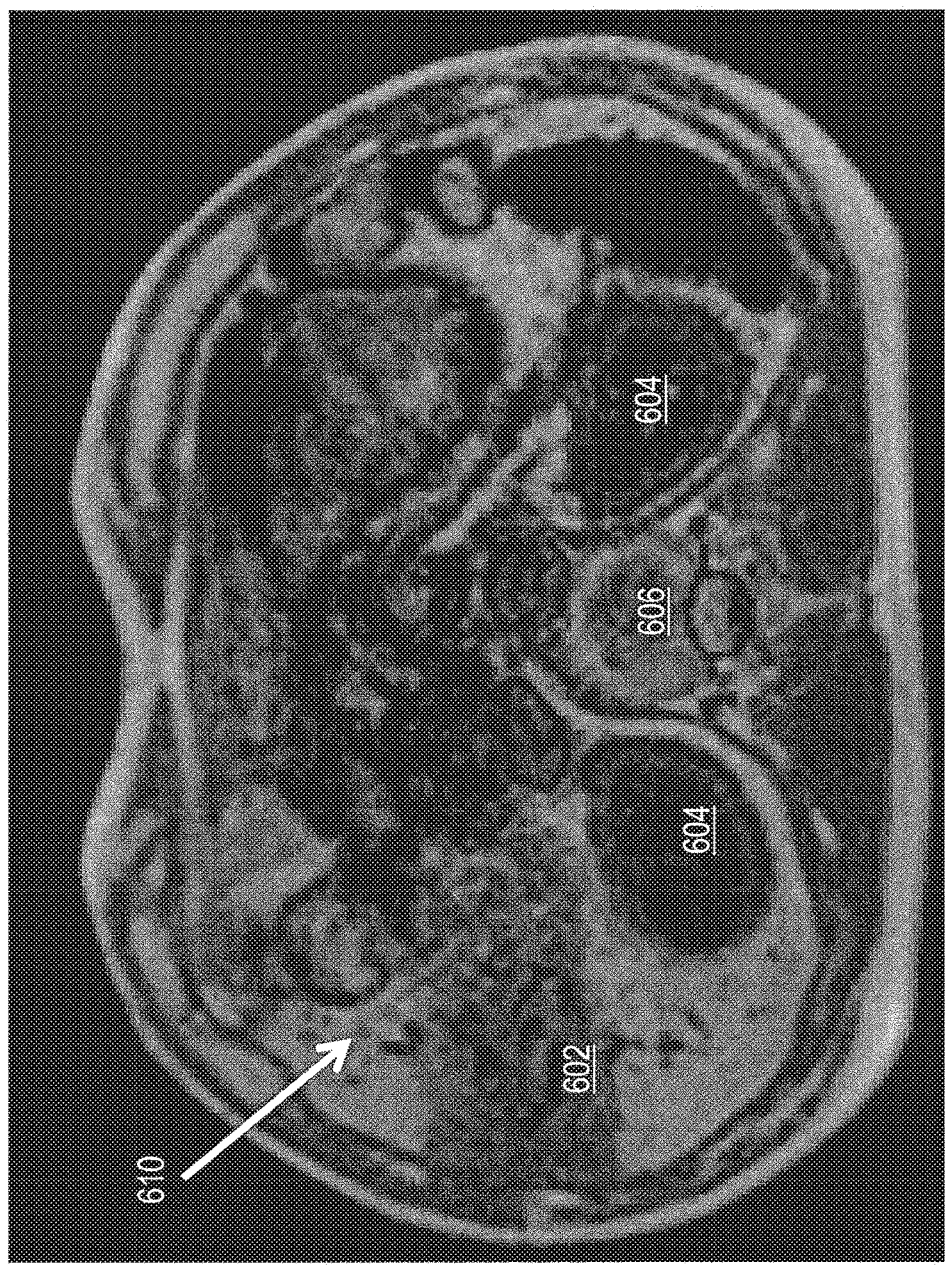
FIG. 6 shows a first MRI scan image illustrating a $T_1$-weighted scan result.
Figure 7:
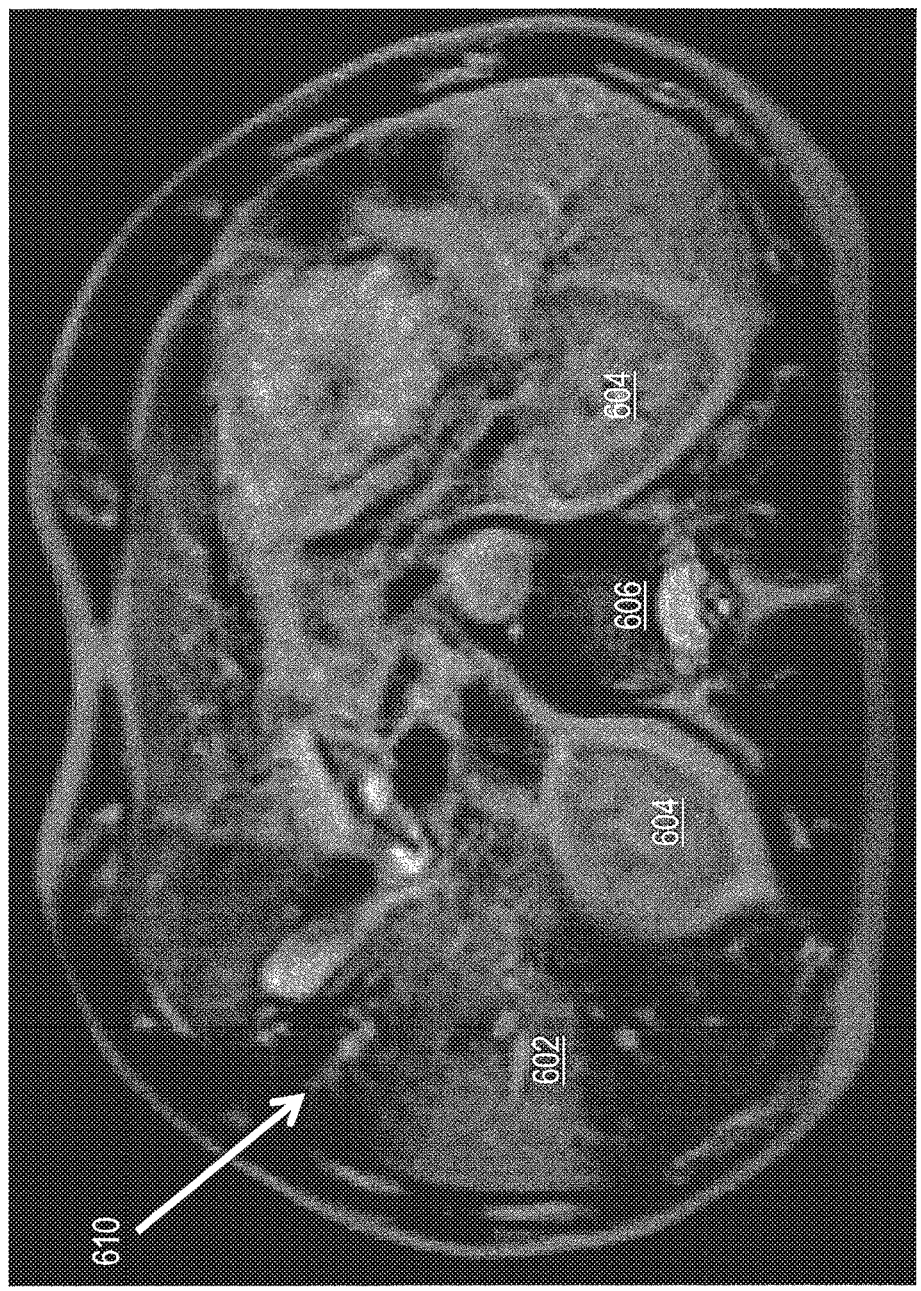
FIG. 7 shows a second MRI scan image illustrating a $T_2$-weighted scan result.

FIG. 6 and FIG. 7 show two MRI scan images 600, 700 of same part of a subject patient taken closely in time. The scan image 600 of FIG. 6 shows a $T_1$-weighted scan in which areas containing more free hydrogen (e.g. tissues having higher water content) are represented more darkly than areas containing more fixed hydrogen (e.g. fatty tissue). The scan image 700 of FIG. 7 shows a $T_2$-weighted scan in which areas containing more fixed hydrogen (e.g. fatty tissue) are represented more darkly than areas containing more free hydrogen (e.g. tissues having higher water content). The scan images 600, 700 show a section through the subject patient's abdomen and show the liver 602, kidneys 604, and spinal column 606 among other features. The liver 602 contains a high amount of fatty tissue, and is therefore less dark in the scan image 600 showing the $T_1$-weighted scan result than in the scan image 607 showing the $T_2$-weighted scan result. Similarly, the spinal column is lighter in FIG. 6 than in FIG. 7 while the kidneys, having a larger water content, are darker in FIG. 6 than in FIG. 7. Also depicted in FIG. 6 and FIG. 7 is a radiation pathway 610 over which radiation treatment was delivered to the patient.

As seen in both FIG. 6 and FIG. 7, the scan images 600, 700 indicate an increase in fluid along the radiation pathway 610, which appears as a darker line in the lighter liver 602 in the $T_1$-weighted scan of FIG. 6 and as a lighter line in the darker liver in the $T_2$-weighted scan of FIG. 7. This increased fluid is the result of edema caused by cell damage in tissues affected by the radiation treatment.

Prior to the present disclosure, a conventional approach to observations of such edema was to ignore or attempt to correct for this "artifact" that generally considered as an interference to analysis of underlying pathologies that necessitated the radiation treatment. In contrast, the current subject matter utilizes a quantification of edema based on one or more MRI scans of a treated area of a patient to at least estimate an effect of a radiation treatment dose on both a target structure (e.g. a tumor or other diseased tissue) and the surrounding tissues. The edema quantified in this manner is generally considered to be acute, transient edema resulting from cell death in the tissue through which the beam had passed.

In practice, implementations of the current subject matter can include quantification of a ratio of $T_1$-weighted and $T_2$-weighted scans to determine, or at least estimate, a free hydrogen ratio as a function of spatial location within a patient's tissues. Increases in the estimated free hydrogen ratio can be interpreted as an indicator of increased edema in the patient's tissues. In this manner changes in edema can be used as a proxy for estimation of an amount of cell damage or death is occurring in a given tissue region of the patient. As noted above, cell damaged or destruction by radiation-induced (as well as other) trauma results in initiator cells (e.g. macrophages, dendritic cells, histiocytes, Kupffer cells, mastocytes, etc.) releasing inflammatory mediators responsible for the clinical signs of inflammation, including but not limited to edema (exudation of plasma proteins and fluid into the tissue). This fluid exudation can be detected, at least on a differential basis, consistent with implementations of the current subject matter by using MRI scans to detect changes in free hydrogen content in tissues. It is possible to characterize such changes using one or more of the scans discussed above. In other examples, two or more scans can be combined to create a ratio metric representative of the free hydrogen content in a patient's tissues as a function of spatial position with the tissues.

Figure 8:
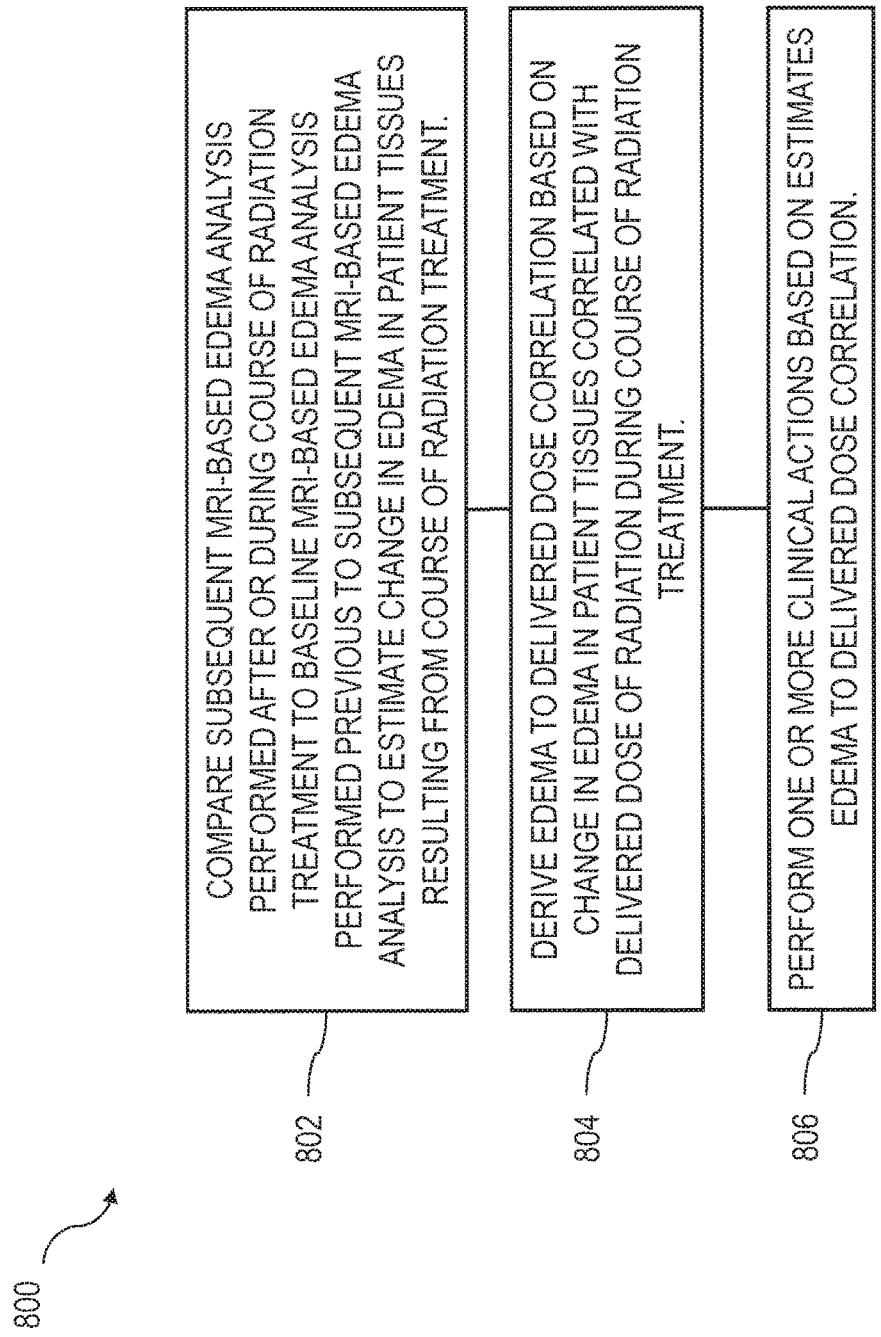
FIG. 8 shows a process flow diagram illustrating aspects of a method having one or more features consistent with implementations of the current subject matter.

Consistent with one or more implementations of the current subject matter, a method as illustrated in the process flow chart 800 of FIG. 8 can include the following features. At 802, a subsequent edema analysis (e.g. a subsequent MRI-based edema analysis) performed after or during at least part of a course of radiation treatment are compared to a baseline edema analysis (e.g. a baseline MRI-based edema analysis) performed previous to the subsequent edema analysis to estimate a change in edema in patient tissues resulting from the course of radiation treatment. In some implementations of the current subject matter, the subsequent edema analysis and the baseline edema analysis can be MRI scans, which can provide estimates of fluid content in cells.

As discussed above, for example, the baseline and subsequent edema analyses can each include one or more MRI scans. In some implementations of the current subject matter, the one or more MRI scans can include both $T_1$-weighted and $T_2$-weighted scans, and a ratio of the results of these scans can be prepared for each of the baseline and subsequent scan. The change in edema can be derived (e.g. estimated, calculated, determined, etc.) based on a differential analysis of the subsequent scan and the baseline scan to determine changes occurring during the course of radiation treatment. In some examples, an amount of free hydrogen can be quantified in the subsequent scan relative to the baseline scan, and a change in the relative amount of free hydrogen can be used as a proxy for the change in edema in the patient's tissue.

A baseline scan can act as a reference for comparison with the one or more subsequent MRI scans taken during or after at least one radiation fraction delivered to the patient in the course of radiation treatment. In other words, the baseline scan accounts for the presence of existing edema, for example edema resulting from original pathologies, other trauma, etc. At least one subsequent MRI scan is taken during the course of treatment (e.g. one or more of intra-fraction or inter-fraction MRI scans), and changes occurring in the patient's tissue between the baseline and subsequent scans can be quantified. In some examples, this quantifying can be accomplished via a differential imaging approach to indicate changes in intensity of MRI signals from patient tissue.

A single type of MRI scan can be used for the baseline and at least one subsequent scan, and changes in the MRI response to this kind of scan can be quantified between the baseline and subsequent scan. Alternatively, as noted above, each scan can include a ratio of two or more types of scans, such as for example $T_1$-weighted and $T_2$-weighted scans. Because edema generally result in an increase in fluid as normal cell damage or cell death recovery mechanisms involve flushing of dead or damaged cell material away via liquids that have a higher water (and therefore high free hydrogen) content. In some variations, a baseline scan can be taken prior to any treatment and then used in comparisons with subsequent scans taken during or between radiation dose fractions delivered to the patient. In other variations, a series of scans can be used, and differential analysis can be applied between two or more scans in the series, possible but not necessarily using a scan collected prior to the commencement of a course of radiation treatment as the baseline scan.

At 804, an edema to delivered dose correlation is derived based on the change in edema in the patient tissue correlated with a delivered dose of radiation during the course of radiation treatment. In other words, one or more calculations or models of physical dose delivery can be applied to derive (e.g. estimate, calculate, determine, etc.) one or more of an amount of radiation actually delivered to the patient tissue, an expected amount of radiation delivered to the patient tissue, or the like. The derived amount of radiation actually delivered or expected to have been delivered can optionally be based on one or more inputs. In some variations, a pre-radiation treatment plan can provide these data. In other variations, a combined MRI and radiation delivery approach (e.g. as described in co-owned U.S. Pat. No. 7,907,987) can be used in calculating a more accurate measure of received doses of radiation to diseased tissue and other tissue structures based on intra-fraction motions of the patient, the patient's organs, etc.

The correlating of the change in edema in the patient tissue with the delivered dose (or the expected delivered dose) can involve quantifying how the change in edema corresponds to an expected outcome for the diseased tissue and surrounding tissues relative to an expected value (e.g. an expected response of tissue to the amount of delivered radiation). The expected value can be calculated empirically, experimentally, through the application of one or more theoretical models, or the like, or through the combination of one or more such approaches.

At 806, one or more clinical actions are performed based on the edema to delivered dose correlation. The clinical actions can include one or more of a variety of actions. For example, if edema a patient experiences, in particular edema in tissue structures other than the target diseased tissue, exceeds an expected value by more than a threshold amount, the course of treatment can be stopped for further analysis, the radiation delivery system can be inspected to ascertain any malfunctioning components, a clinician can be alerted by a user interface or some other automated method, an amount of radiation delivered in a next fraction can be reduced, etc. In other examples, if the edema a patient experiences, in particular edema in target diseased tissue, is less than an expected value by more than a threshold amount, the course of treatment can likewise be stopped for further analysis, the radiation delivery system can be inspected to ascertain any malfunctioning components, a clinician can be alerted by a user interface or some other automated method, an amount of radiation delivered in a next fraction can be increased (assuming, for example that edema experienced by the patient in tissue structures other than the target diseased tissue is within some acceptable limit), etc.

As discussed above, MRI scan data analyzed differentially over some period of time that includes at least one delivery of a radiation therapy dose can be used to derive at least an estimate of amount of cell death or damage occurring in the scanned tissue. Such data can be expressed in a variety of ways, including but not limited to a visual depiction, a numerical expression, or the like representing intensity as a function of location within a patient's tissues. For example, in the case of a ratio of $T_1$-weighted and $T_2$-weighted scans used as a proxy for free hydrogen content in scanned tissues, the differential changes in the ratio of these two scans can be presented as a function of location. This presentation can include use of voxels on a 2D map or other image of a part of the patient's tissues in the vicinity of the targeted diseased tissue to visually depict cell death or damage occurring over a course of treatment.

Increasing ratios of free hydrogen can be used as a proxy for increasing amounts of damaged tissue in a given location, which can be clinically useful as a virtual, relative dosimeter for absorbed active radiation dose. In this manner, a measure can be provided of how much of a treatment impact the radiation therapy has had on the targeted diseased tissue how severely other surrounding tissues have been impacted, etc. Accordingly, implementations of the current subject matter can assist in medically managing a patient undergoing radiation treatment. Comparison of the "expected" outcomes of a dosimetry plan with actual observed changes in edema can allow a clinician to better estimate how a specific patient is responding to the specific course of radiation treatment.

Figure 9:
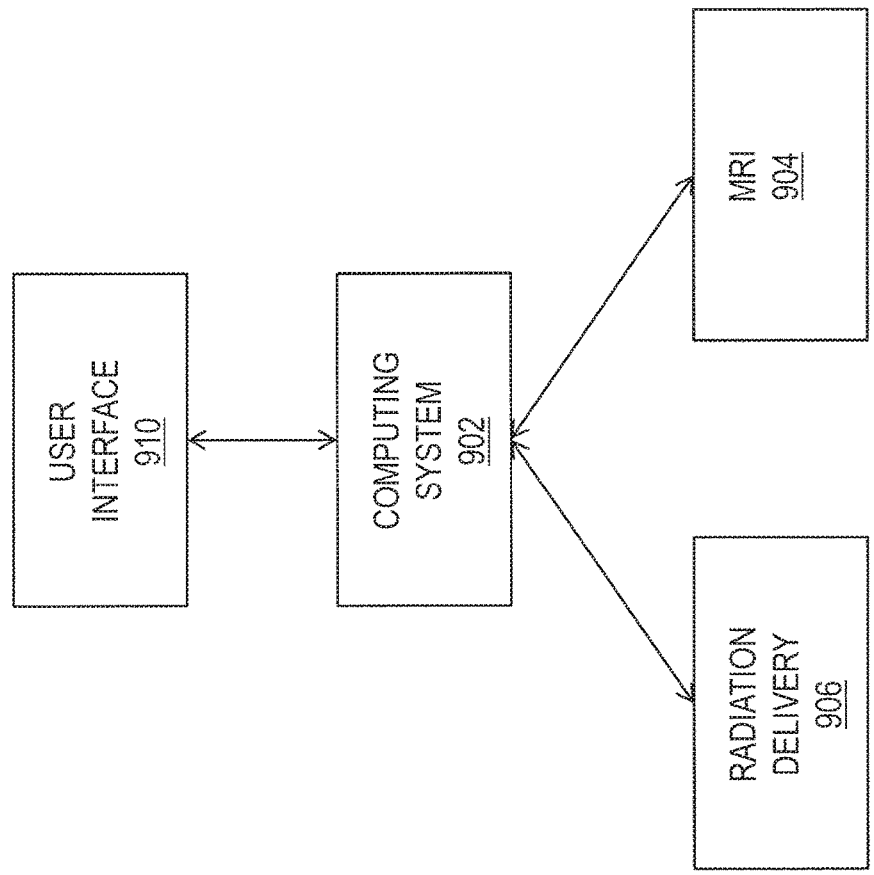
FIG. 9 shows a diagram illustrating features of a system consistent with implementations of the current subject matter.

FIG. 9 shows a schematic diagram of a system 900 having one or more features in common with implementations of the current subject matter. A computing system 902 can be in communication with an MRI system 904, and optionally with a radiation delivery system 906. A user interface can optionally include displays, user input devices, etc. as well as other examples discussed below for conveying information to a clinician or other user and/or for receiving information inputs. The computing system 902 can optionally be part of or otherwise integrated into the MRI system 904 and/or to the radiation delivery system. In the example of FIG. 1 through FIG. 5, the computing system 902, the MRI system 904, and the radiation delivery system 906 can all be integrated. In some examples, the radiation delivery system 906 can include its own computing system, such as for example a dose planning system running dose planning software. Communication of data between the various components of the system 900 can be accomplished over any data transfer connections (networks, computer buses, etc.). The computing system 902 can optionally include a programmable processor that executes one or more software modules that implement one or more of the features discussed above.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like. A computer remote from an analyzer can be linked to the analyzer over a wired or wireless network to enable data exchange between the analyzer and the remote computer (e.g. receiving data at the remote computer from the analyzer and transmitting information such as calibration data, operating parameters, software upgrades or updates, and the like) as well as remote control, diagnostics, etc. of the analyzer.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system comprising:
   at least one programmable processor; and
   a non-transitory machine-readable medium storing instructions which, when executed by the at least one programmable processor, cause the at least one programmable processor to perform operations comprising:
   capturing baseline MRI scans and, during a radiation treatment, subsequent intra-fraction MRI scans, the baseline MRI scans and subsequent intra-fraction MRI scans including at least one of a T1-weighted or a T2-weighted scan; and
   determining one or more changes in MRI signal due to inflammation of patient tissues based on changes in T1, in T2, or both, between the baseline MRI scans and subsequent intra-fraction MRI scans.

2. The system of claim 1, wherein a decrease in T1, increase in T2, or both indicates an increase in the inflammation.

3. The system of claim 1, the operations further comprising:
   calculating an inflammation distribution based on the determined changes in the MRI signal.

4. The system of claim 3, the operations further comprising:
   generating an inflammation volume histogram based on the inflammation distribution.

5. The system of claim 3, the operations further comprising:
   correlating the inflammation distribution to known toxicities; and
   generating a prediction of toxicity based on the correlation.

6. The system of claim 3, the operations further comprising:
   correlating the inflammation distribution to known patient outcomes; and
   generating a prediction of a patient outcome based on the correlation.

7. The system of claim 1, wherein the T2-weighted MRI scan includes utilizing a gradient echo sequence.

8. A non-transitory machine-readable medium storing instructions which, when executed by the at least one programmable processor, cause the at least one programmable processor to perform operations comprising:
   capturing baseline MRI scans and, during a radiation treatment, subsequent intra-fraction MRI scans, the baseline MRI scans and subsequent intra-fraction MRI scans including at least one of a T1-weighted or a T2-weighted scan; and
   determining one or more changes in MRI signal due to inflammation of patient tissues based on changes in T1, in T2, or both, between the baseline MRI scans and subsequent intra-fraction MRI scans.

9. The machine-readable medium of claim 8, wherein a decrease in T1, increase in T2, or both indicates an increase in the inflammation.

10. The machine-readable medium of claim 8, the operations further comprising:
    calculating an inflammation distribution based on the determined changes in the MRI signal.

11. The machine-readable medium of claim 10, the operations further comprising:
    generating an inflammation volume histogram based on the inflammation distribution.

12. The machine-readable medium of claim 10, the operations further comprising:
    correlating the inflammation distribution to known toxicities; and
    generating a prediction of toxicity based on the correlation.

13. The machine-readable medium of claim 10, the operations further comprising:
    correlating the inflammation distribution to known patient outcomes; and
    generating a prediction of a patient outcome based on the correlation.

14. The machine-readable medium of claim 8, wherein the T2-weighted MRI scan includes utilizing a gradient echo sequence.

* * * * *